(12) United States Patent
Mazar et al.

(10) Patent No.: US 7,127,300 B2
(45) Date of Patent: Oct. 24, 2006

(54) METHOD AND APPARATUS FOR ENABLING DATA COMMUNICATION BETWEEN AN IMPLANTABLE MEDICAL DEVICE AND A PATIENT MANAGEMENT SYSTEM

(75) Inventors: Scott T. Mazar, Inver Grove Heights, MN (US); Yatheendhar D. Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 194 days.

(21) Appl. No.: 10/328,653

(22) Filed: Dec. 23, 2002

(65) Prior Publication Data

US 2004/0122488 A1 Jun. 24, 2004

(51) Int. Cl.
*A61B 1/20* (2006.01)
(52) U.S. Cl. .................................................. 607/60
(58) Field of Classification Search ............... 607/27, 607/32, 60; 600/300; 128/903, 904; 340/442; 705/71; 713/182
See application file for complete search history.

(56) References Cited

U.S. PATENT DOCUMENTS

| | | | |
|---|---|---|---|
| 4,561,443 A | 12/1985 | Hogrefe et al. | 128/419 |
| 4,658,831 A | 4/1987 | Reinhard et al. | 128/697 |
| 4,681,111 A | 7/1987 | Silvian | 128/419 |
| 4,705,043 A | 11/1987 | Imran | 128/419 |
| 4,757,816 A | 7/1988 | Ryan et al. | 128/419 |
| 4,793,353 A | 12/1988 | Borkan | 128/421 |
| 4,809,697 A | 3/1989 | Causey, III et al. | 128/419 |
| 4,932,408 A | 6/1990 | Schaldach | 128/419 |
| 4,947,407 A | 8/1990 | Silvian | 375/94 |
| 4,969,464 A | 11/1990 | Callaghan et al. | 128/419 |
| 5,058,581 A | 10/1991 | Silvian | 128/419 |
| 5,081,987 A | 1/1992 | Nigam | 120/419 |
| 5,113,869 A | 5/1992 | Nappholz et al. | 128/696 |
| 5,117,825 A | 6/1992 | Grevious | 128/419 |
| 5,137,022 A | 8/1992 | Henry | 128/419 |
| 5,241,961 A | 9/1993 | Henry | 607/32 |
| 5,292,343 A | 3/1994 | Blanchette et al. | 607/32 |
| 5,331,966 A | 7/1994 | Bennett et al. | 128/696 |
| 5,336,245 A | 8/1994 | Adams et al. | 607/32 |
| 5,350,411 A | 9/1994 | Ryan et al. | 607/32 |
| 5,381,798 A | 1/1995 | Burrows | 128/696 |
| 5,383,915 A | 1/1995 | Adams | 607/60 |

(Continued)

FOREIGN PATENT DOCUMENTS

EP 0 554 955 A1 8/1993

*Primary Examiner*—George Manuel
(74) *Attorney, Agent, or Firm*—Schwegman, Lundberg, Woessner & Kluth, P.A.

(57) ABSTRACT

Embodiments of the invention provide methods, systems, and devices for enabling data communication between an IMD and a host computer. In one embodiment, a device is provided that comprises a frequency and protocol agile transceiver capable of communicating with an IMD via a short range communications link and with a host computer via a long range wireless communications link. The transceiver may be utilized by the device to retrieve clinical data stored in the IMD and to transmit the clinical data directly to the host computer via the long range wireless communications link. An apparatus is provided according to another embodiment of the invention that comprises an interface between an IMD and a communications device, such as a wireless telephone or a two-way wireless pager. The interface can communicate directly with the IMD to retrieve clinical data stored in the IMD and can utilize the communications device to transmit the clinical data to a host computer.

14 Claims, 10 Drawing Sheets

U.S. PATENT DOCUMENTS

| | | | |
|---|---|---|---|
| 5,413,594 A | 5/1995 | Williams | 607/32 |
| 5,415,181 A | 5/1995 | Hogrefe et al. | 128/736 |
| 5,458,122 A | 10/1995 | Hethuin | 128/696 |
| 5,476,485 A | 12/1995 | Weinberg et al. | 607/28 |
| 5,481,262 A | 1/1996 | Urbas et al. | 340/870.17 |
| 5,509,927 A | 4/1996 | Epstein et al. | 607/32 |
| 5,522,865 A | 6/1996 | Schulman et al. | 607/56 |
| 5,549,654 A | 8/1996 | Powell | 607/32 |
| 5,626,630 A | 5/1997 | Markowitz et al. | 607/60 |
| 5,629,678 A | 5/1997 | Gargano et al. | 340/573 |
| 5,630,836 A | 5/1997 | Prem et al. | 607/61 |
| 5,674,249 A | 10/1997 | De Coriolis et al. | 607/5 |
| 5,683,432 A | 11/1997 | Goedeke et al. | 607/32 |
| 5,713,937 A | 2/1998 | Nappholz et al. | 607/30 |
| 5,720,770 A | 2/1998 | Nappholz et al. | 607/30 |
| 5,741,315 A | 4/1998 | Lee et al. | 607/60 |
| 5,743,267 A | 4/1998 | Nikolic et al. | 128/673 |
| 5,752,976 A | 5/1998 | Duffin et al. | 607/32 |
| 5,752,977 A | 5/1998 | Grevious et al. | 607/32 |
| 5,759,199 A | 6/1998 | Snell et al. | 607/60 |
| 5,766,232 A | 6/1998 | Grevious et al. | 607/60 |
| 5,769,876 A | 6/1998 | Silvian | 607/60 |
| 5,772,586 A | 6/1998 | Heinonen et al. | 600/300 |
| 5,774,501 A | 6/1998 | Halpern et al. | 375/279 |
| 5,791,342 A | 8/1998 | Woodard | 128/630 |
| 5,792,207 A | 8/1998 | Dietrich | 607/32 |
| 5,814,089 A | 9/1998 | Stokes et al. | 607/32 |
| 5,836,983 A | 11/1998 | Weijand et al. | 607/9 |
| 5,843,133 A | 12/1998 | Routh et al. | 607/14 |
| 5,843,139 A | 12/1998 | Goedeke et al. | 607/32 |
| 5,861,014 A | 1/1999 | Familoni | 607/40 |
| 5,861,018 A | 1/1999 | Feierbach | 607/60 |
| 5,862,803 A | 1/1999 | Besson et al. | 129/696 |
| 5,889,474 A | 3/1999 | LaDue | 340/825 |
| 5,899,928 A | 5/1999 | Sholder et al. | 607/27 |
| 5,899,931 A | 5/1999 | Deschamp et al. | 607/60 |
| 5,917,414 A | 6/1999 | Oppelt et al. | 340/573.1 |
| 5,919,214 A | 7/1999 | Ciciarelli et al. | 607/32 |
| 5,935,078 A | 8/1999 | Feierbach | 600/509 |
| 5,944,659 A | 8/1999 | Flach et al. | 600/300 |
| 5,957,861 A | 9/1999 | Combs et al. | 600/547 |
| 5,999,857 A | 12/1999 | Weijand et al. | 607/60 |
| 6,083,248 A | 7/2000 | Thompson | 607/30 |
| 6,093,146 A | 7/2000 | Filangeri | 600/300 |
| 6,115,636 A | 9/2000 | Ryan | 607/60 |
| 6,141,584 A | 10/2000 | Rockwell et al. | 607/5 |
| 6,170,488 B1 | 1/2001 | Spillman, Jr. et al. | 128/899 |
| 6,185,452 B1 | 2/2001 | Schulman et al. | 604/20 |
| 6,200,264 B1 | 3/2001 | Satherley et al. | 600/300 |
| 6,203,495 B1 | 3/2001 | Bardy | 600/301 |
| 6,206,835 B1 | 3/2001 | Spillman, Jr. et al. | 600/485 |
| 6,208,894 B1 | 3/2001 | Schulman et al. | 607/2 |
| 6,213,942 B1 | 4/2001 | Flach et al. | 600/300 |
| 6,216,038 B1 | 4/2001 | Hartlaub et al. | 607/31 |
| 6,221,011 B1 | 4/2001 | Bardy | 600/300 |
| 6,223,083 B1 | 4/2001 | Rosar | 607/60 |
| 6,236,889 B1 | 5/2001 | Soykan et al. | 607/30 |
| 6,240,317 B1 | 5/2001 | Villaseca et al. | 607/60 |
| 6,250,309 B1 | 6/2001 | Krichen et al. | 128/899 |
| 6,261,230 B1 | 7/2001 | Bardy | 600/300 |
| 6,263,245 B1 | 7/2001 | Snell | 607/60 |
| 6,263,246 B1 | 7/2001 | Goedeke et al. | 607/60 |
| 6,263,247 B1 | 7/2001 | Mueller et al. | 607/60 |
| 6,270,457 B1 | 8/2001 | Bardy | 600/300 |
| 6,289,238 B1 | 9/2001 | Besson et al. | 600/509 |
| 6,292,698 B1 | 9/2001 | Duffin et al. | 607/32 |
| 6,295,466 B1 | 9/2001 | Ishikawa et al. | 600/509 |
| 6,298,271 B1 | 10/2001 | Weijand | 607/60 |
| 6,300,903 B1 | 10/2001 | Richards et al. | 342/450 |
| 6,304,788 B1 | 10/2001 | Eady et al. | 700/86 |
| 6,319,200 B1 | 11/2001 | Lai et al. | 600/300 |
| 6,329,929 B1 | 12/2001 | Weijand et al. | 340/870.25 |
| 6,345,203 B1 | 2/2002 | Mueller et al. | 607/60 |
| 6,349,234 B1 | 2/2002 | Pauly et al. | 607/60 |
| 6,363,282 B1 | 3/2002 | Nichols et al. | 607/30 |
| 6,418,346 B1 | 7/2002 | Nelson et al. | 607/59 |
| 6,442,432 B1 | 8/2002 | Lee | 607/59 |
| 6,442,433 B1 | 8/2002 | Linberg | 607/60 |
| 6,477,242 B1 | 11/2002 | Freeny, Jr. | 379/93.24 |
| 6,480,745 B1 | 11/2002 | Nelson et al. | 607/60 |
| 6,763,269 B1* | 7/2004 | Cox | 607/60 |
| 6,825,758 B1* | 11/2004 | Laitsaari | 340/442 |
| 6,880,085 B1* | 4/2005 | Balczewski et al. | 713/182 |
| 2001/0012955 A1 | 8/2001 | Goedeke et al. | 607/27 |
| 2001/0023360 A1 | 9/2001 | Nelson et al. | 607/60 |
| 2001/0025137 A1 | 9/2001 | Webb et al. | 600/300 |
| 2001/0025189 A1 | 9/2001 | Haueter et al. | 607/62 |
| 2001/0027331 A1 | 10/2001 | Thompson | 607/60 |
| 2001/0027349 A1 | 10/2001 | Eady et al. | 700/17 |
| 2001/0029321 A1 | 10/2001 | Beetz et al. | 600/300 |
| 2001/0031998 A1 | 10/2001 | Nelson et al. | 607/60 |
| 2001/0037056 A1 | 11/2001 | Nunome | 600/300 |
| 2001/0039372 A1 | 11/2001 | Yasushi et al. | 600/300 |
| 2001/0044588 A1 | 11/2001 | Mault | 600/549 |
| 2001/0047125 A1 | 11/2001 | Quy | 600/300 |
| 2001/0051764 A1 | 12/2001 | Bardy | 600/300 |
| 2001/0051787 A1 | 12/2001 | Haller et al. | 604/66 |
| 2002/0013517 A1 | 1/2002 | West et al. | 600/300 |
| 2002/0013518 A1 | 1/2002 | West et al. | 600/300 |
| 2002/0013538 A1 | 1/2002 | Teller | 600/549 |
| 2002/0013613 A1 | 1/2002 | Haller et al. | 607/60 |
| 2002/0013614 A1 | 1/2002 | Thompson | 607/60 |
| 2002/0019584 A1 | 2/2002 | Schulze et al. | 600/300 |
| 2002/0019586 A1 | 2/2002 | Teller et al. | 600/300 |
| 2002/0028988 A1 | 3/2002 | Suzuki et al. | 600/300 |
| 2002/0032470 A1 | 3/2002 | Linberg | 607/60 |
| 2002/0040234 A1 | 4/2002 | Linberg | 607/32 |
| 2002/0052539 A1 | 5/2002 | Haller et al. | 600/300 |
| 2002/0072785 A1 | 6/2002 | Nelson et al. | 607/60 |
| 2002/0082665 A1 | 6/2002 | Haller et al. | 607/60 |
| 2002/0095196 A1 | 7/2002 | Linberg | 607/60 |
| 2002/0111542 A1 | 8/2002 | Warkentin et al. | 600/300 |
| 2003/0014372 A1* | 1/2003 | Wheeler et al. | 705/71 |
| 2004/0078067 A1* | 4/2004 | Thompson et al. | 607/60 |
| 2004/0176822 A1* | 9/2004 | Thompson et al. | 607/60 |

\* cited by examiner

METHOD AND APPARATUS FOR ENABLING DATA COMMUNICATION BETWEEN AN IMPLANTABLE MEDICAL DEVICE AND A PATIENT MANAGEMENT SYSTEM

TECHNICAL FIELD

This application relates generally to patient management systems, and particularly, but not by way of limitation, to an interface device for coupling an implantable medical device to a host computer utilized in a patient management system.

BACKGROUND OF THE INVENTION

Management of patients with chronic disease consumes a significant proportion of the total health care expenditure in the United States. Many of these diseases are widely prevalent and have significant annual incidences as well. Heart Failure prevalence alone is estimated at over 5.5 million patients in 2000 with incidence rates of over half a million additional patients annually, resulting in a total health care burden in excess of $20 billion. Heart Failure, like many other chronic diseases such as Asthma, Chronic Obstructive Pulmonary Disease ("COPD"), Chronic Pain, and Epilepsy is event driven, where acute de-compensations result in hospitalization. In addition to causing considerable physical and emotional trauma to the patient and family, event driven hospitalizations consume a majority of the total health care expenditure allocated to the treatment of heart failure.

An interesting fact about the treatment of acute de-compensation is that hospitalization and treatment occurs after the event (de-compensation) has happened. However, most Heart Failure patients exhibit prior non-traumatic symptoms, such as steady weight gain, in the weeks or days prior to the de-compensation. If the attending physician is made aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise regimens. Such intervention is usually effective in preventing the de-compensation episode and thus avoiding hospitalization.

In order to provide early detection of symptoms that may signal an increased likelihood of a traumatic medical event, patients may receive implantable medical devices ("IMDs") that have the ability to measure various body characteristics. For instance, IMDs are currently available that provide direct measurement of electrical cardiac activity, physical motion, temperature, and other clinical parameters. The data collected by these devices is typically retrieved from the device through interrogation.

Some IMDs communicate with a repeater located in the patient's home via a short range wireless communications link. The repeater interrogates the IMD and retrieves the clinical data stored within the IMD. The repeater then establishes a connection with a host computer or patient management system and transmits the clinical data.

While the use of a repeater is convenient for a patient while located near the repeater, no data can be transmitted from the IMD to the repeater if the IMD is out of range. Therefore, if the patient is away from home, no data can be communicated to the host computer system via the repeater. This can be extremely inconvenient, and even dangerous, for the patient if a medically significant event occurs while the IMD is out of range of the repeater.

Therefore, in light of the above, there is a need for a method and apparatus for enabling data communication between an IMD and a host computer that enables communication between the IMD and the host computer in a manner that does not require proximity to a fixed repeater device. There is a further need for a method and apparatus for enabling data communication between an IMD and a host computer that utilizes a portable communications device for directly communicating with the host computer.

SUMMARY OF THE INVENTION

Embodiments of the present invention solve the above-described problems by providing a method and apparatus for enabling communication between an IMD and a host computer that do not require the use of a fixed location repeater device. Embodiments of the present invention also solve the above-described problems by enabling communication between an IMD and a host computer in a manner that utilizes a portable wireless communications device that can establish a data connection with the host computer directly through a long range wireless communications link.

According to one actual embodiment of the present invention, an apparatus is provided for enabling communication between an IMD and a host computer operated as a part of a patient management system. The apparatus comprises a frequency and protocol agile transceiver capable of configuring itself for communication with the IMD via a short range wireless communications link and for communication with a host computer via a long range wireless communications link, such as through the wireless telephone network.

The apparatus provided according to one embodiment of the invention also comprises a central processing unit ("CPU"), a memory, and a program capable of configuring the transceiver for communication with the IMD, communicating with the IMD to retrieve clinically significant data stored in the IMD, and of storing the clinical data in the memory. The program is also capable of reconfiguring the transceiver for data communication with the host computer via the long range wireless communications link. Once the transceiver has been configured for communication with the host computer via the long range wireless communications link, the program transmits the clinical data stored in memory to the host computer.

According to another actual embodiment of the present invention, an apparatus is provided that comprises an interface between an IMD and a communications device, such as a wireless telephone or a two-way wireless pager. In particular, the apparatus comprises a transceiver capable of communicating with an IMD via a short range wireless communications link and an input/output interface for communicating with the communications device. Through the transceiver the apparatus can communicate with the IMD and retrieve clinical data stored within the IMD. The apparatus is also operative to establish a communications link with a host computer through the communications device. Once such a communications link has been established, the apparatus can transmit the clinical data to the host computer.

Embodiments of the present invention also include methods and systems for enabling communication between an IMD and a patient management system. These and various other features as well as advantages, which characterize the present invention, will be apparent from a reading of the following detailed description and a review of the associated drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE PREFERRED EMBODIMENT

In the following detailed description, reference is made to the accompanying drawings which form a part hereof, and in which is shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The apparatus and methods described herein are described in the context of a patient management system that provides patient management and device management. As used herein, the phrase "patient management" refers to the process of creating and collecting patient specific information, storing and collating the information, and generating actionable recommendations to enable the predictive management of patients with chronic disease. As used herein, the phrase "device management' refers to the process of leveraging a remote communications infrastructure to provide automatic device follow-ups to collect data, provide therapy, and to determine if remote devices are functioning properly. It should be appreciated that although the embodiments of the invention are described in the context of a patient management system, the embodiments of the invention may be utilized within other operating environments. Additional details regarding the patient management system that provides one operating environment for the embodiments of the invention are provided below with respect to FIGS. 2–4B. Additional details regarding the apparatus provided herein are provided below with respect to FIGS. 1A–1B and 5–8.

Figure 1A:
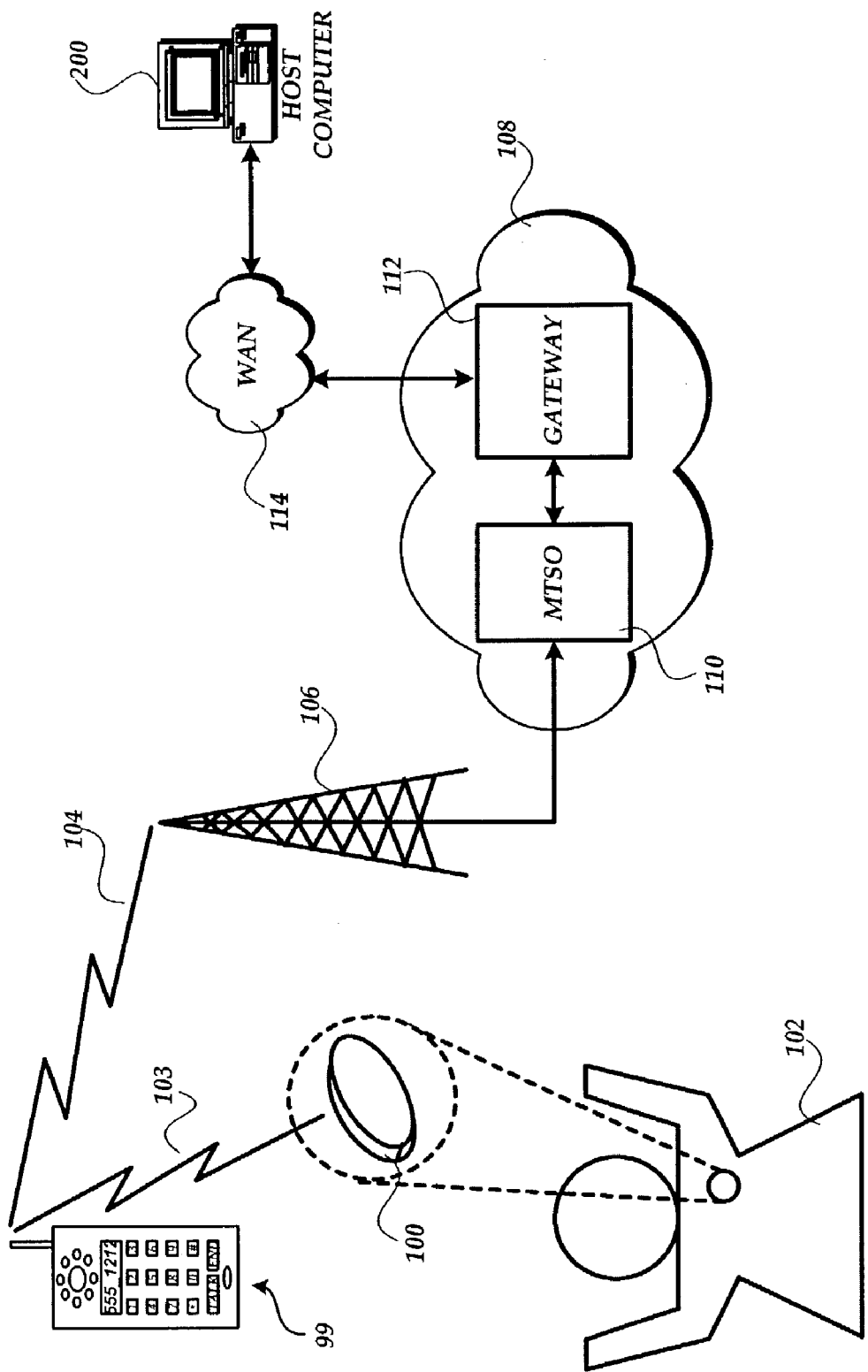
FIGS. 1A and 1B are block diagrams showing the operation of several embodiments of the present invention in an illustrative operating environment.

Turning now to FIG. 1A, one embodiment of the present invention will be described in the context of an illustrative operating environment. As shown in FIG. 1A, an interface device 99 is provided for enabling communication between an IMD 100 and a host computer 200. According to this embodiment, the interface device 99 is capable of communicating with the host computer 200 through a wireless telephone network 108. In particular, the interface device 99 is capable of establishing a long range communications link 104 with a wireless network 108 through a wireless tower 106. The data connection is established through a mobile telephone switching office ("MTSO") 110. A network gateway 112 may also be utilized within the wireless telephone network 108 to enable communication with a wide area network 114 ("WAN"). In the actual embodiment of the present invention described herein, the WAN 114 comprises the Internet. However, other types of WANs known to those skilled in the art may be utilized. In this manner, the interface device 99 can establish a digital data connection with host computer 200 through the wireless telephone network 108 in the same way that a traditional cellular telephone would establish such a connection.

As shown in FIG. 1A, the IMD 100 may be implanted within a patient 102. The IMD 100 has the ability to sense and communicate and may include the ability to provide therapy. In particular, the IMD 100 includes a sensor that allows it to directly measure characteristics of the patient's body. This may include monitoring electrical cardiac activity, physical motion, temperature, heart rate, activity, blood pressure, breathing patterns, wedge-pressure, ejection fractions, blood viscosity, blood chemistry, blood glucose levels, or other patient specific clinical parameters without any patient compliance. The measured clinical data may be stored in a memory of the IMD 100. The IMD 100 also includes a wireless transmitter/receiver unit capable of communicating with the interface device 99 via a short range wireless communications link 103, such as BLUETOOTH, IEEE 802.11b, or other type of short range wireless communications link.

Through the interface device 99, clinical data stored within the IMD 100 can be transmitted to the host computer 200. Status information regarding operation of the IMD 100 may also be sent and software or firmware updates and configuration changes may be received from the host computer 200. As will be described in greater detail below with respect to FIGS. 2–4B, the host computer 200 performs a variety of functions within a patient management system in addition to communicating with the IMD 100.

According to the embodiment of the present invention shown in FIG. 1A, the interface device 99 comprises a wireless digital telephone modified for communication with the IMD 100 and for performing other functions described herein. However, it should be appreciated by those skilled in the art that other types of wireless communication devices may be modified in a similar manner and utilized for communication with the IMD 100 and the host computer 200. For instance, a two-way wireless pager may be similarly modified to communicate with the IMD 100 and to communicate with the host computer 200. Other types of wireless devices may be modified and utilized similarly to facilitate communicating over a variety of pervasive wireless communication network types. Additional details regarding the hardware architecture and operation of the interface device 99 according to this embodiment of the invention will be described below with reference to FIGS. 5 and 6, respectively.

Figure 1B:
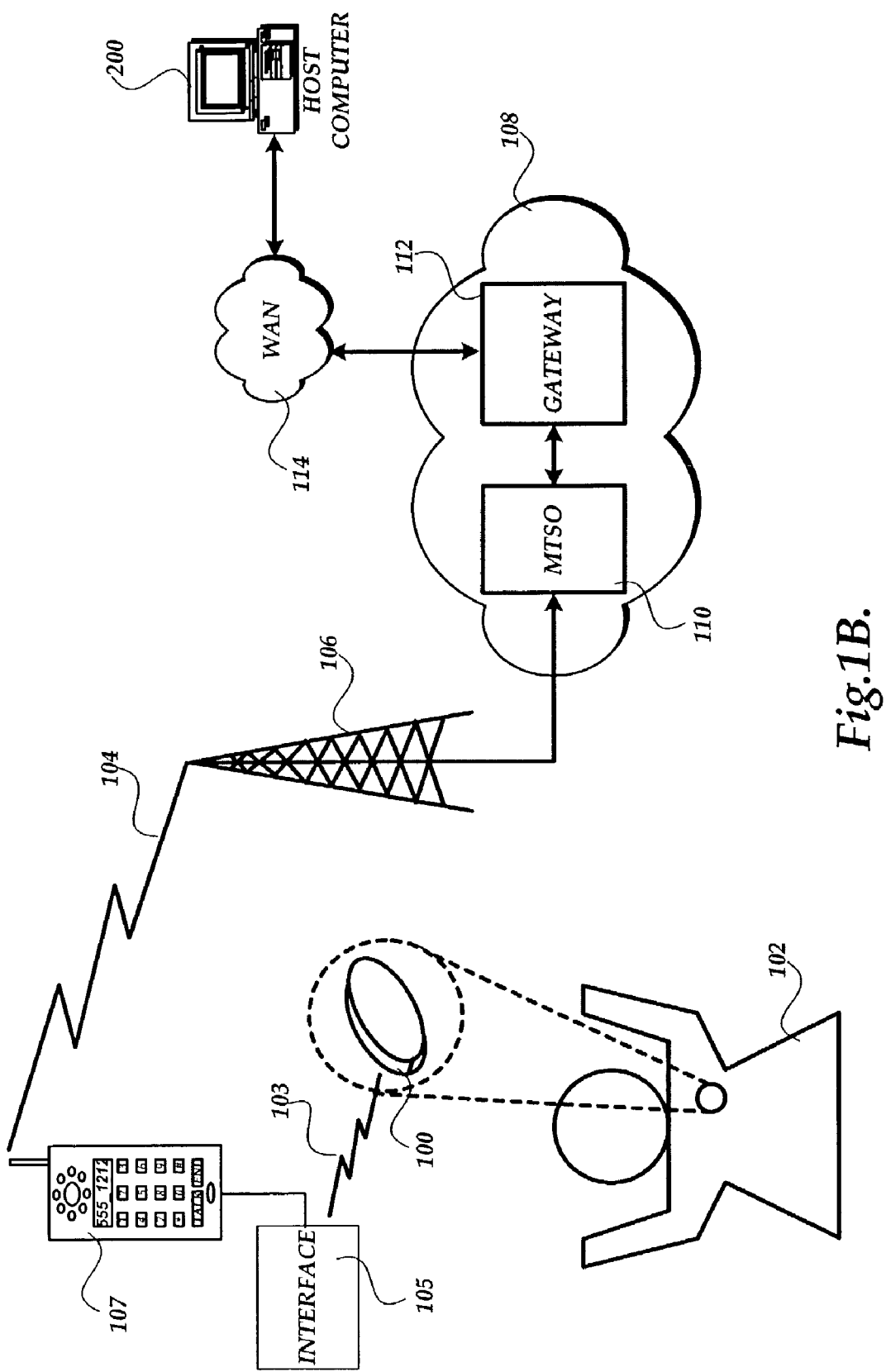

Referring now to FIG. 1B, another embodiment of the present invention will be described. As shown in FIG. 1B, this embodiment of the invention provides an interface device 105 that is capable of communicating with the IMD 100 via a short range communications link 103. As described above, the short range communications link 103 may comprise a BLUETOOTH, IEEE 802.11b, or other type of short range wireless connection. The interface device 105 is also capable of communicating with the host computer 200 via a communications device 107 and a long range communications link 104.

In the embodiment of the present invention shown in FIG. 1B, the communications device 107 comprises a conventional digital wireless telephone. According to this embodiment, communication is established between the interface device 105 and the host computer 200 via the communications device 107, the wireless tower 106, the MTSO 110, the gateway 112, and the WAN 114. However, it should be appreciated by those skilled in the art that other types of wireless communications devices and other types of communication networks may also be utilized, such as a wireless two-way paging network and the like. Additional details regarding the hardware configuration and operation of the interface device 105 will be provided below with reference to FIGS. 7 and 8, respectively.

Figure 2:
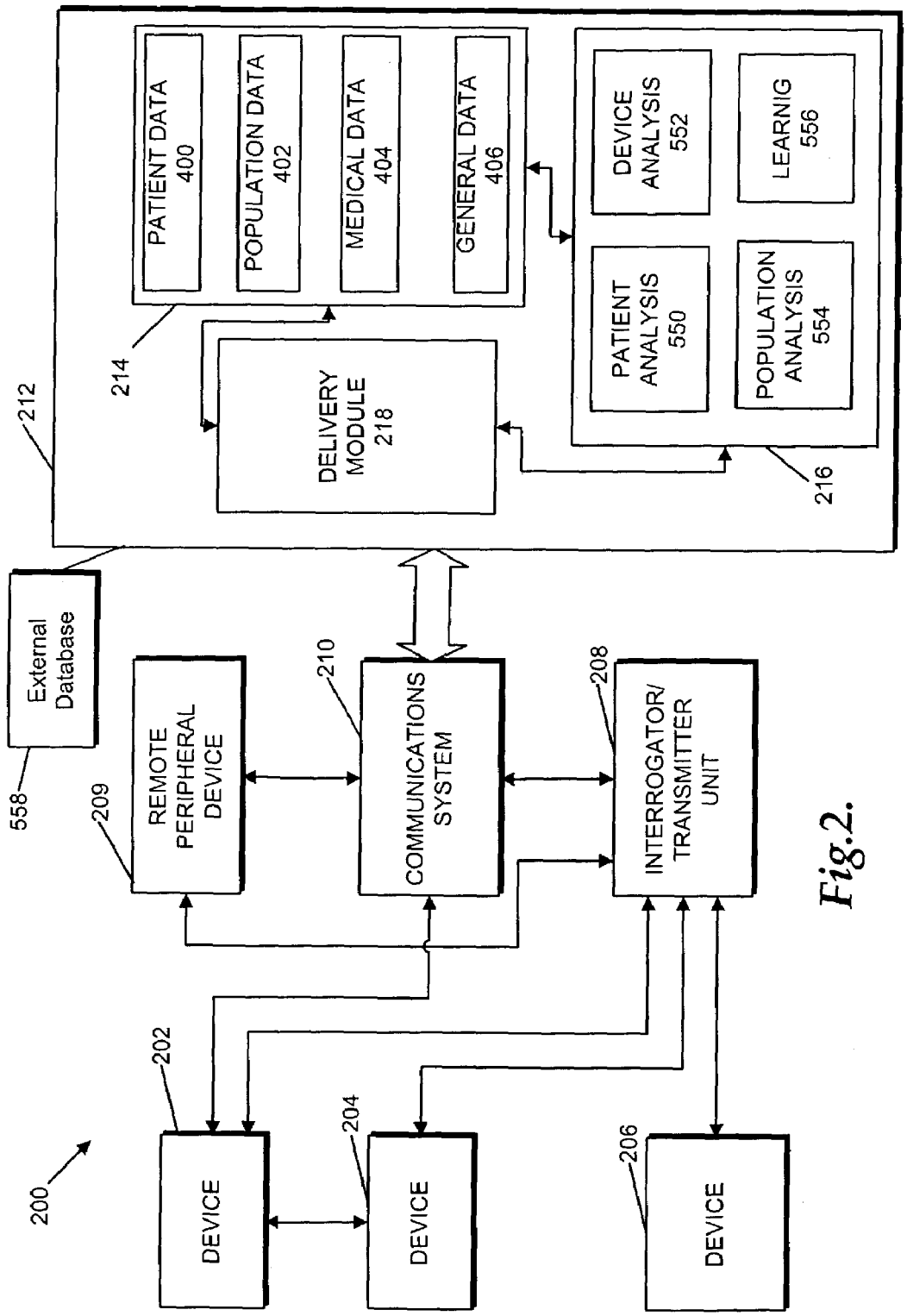
FIG. 2 is a block diagram illustrating an advanced patient management system utilized in one embodiment of the present invention.

FIG. 2 illustrates an example advanced patient management system 200 made in accordance with the present invention. The advanced patient management system 200 can generally include the following components: one or more devices 202, 204, and 206, one or more interrogator/transceiver units 208, a communications system 210, one or more remote peripheral devices 209, and a host 212.

Each component of the advanced patient management system 200 can communicate using the communications system 210. Some components may also communicate directly with one another. For example, devices 202 and 204 may be configured to communicate directly with one another. The various components of the example advanced patient management system 200 illustrated herein are described below.

Devices 202, 204, and 206 can be implantable devices or external devices that may provide one or more of the following functions with respect to a patient: (1) sensing, (2) data analysis, and (3) therapy. For example, in one embodiment, devices 202, 204, and 206 can be implanted or external devices used to measure a variety of physiological, subjective, and environmental conditions of a patient using electrical, mechanical, and/or chemical means. The devices 202, 204, and 206 can be configured to automatically gather data or can require manual intervention by the patient. The devices 202, 204, and 206 can be configured to store data related to the physiological and/or subjective measurements and/or transmit the data to the communications system 210 using a variety of methods, described in detail below. Although three devices 202, 204, and 206 are illustrated in the example embodiment shown, more or fewer devices may be used for a given patient.

The devices 202, 204, and 206 can be configured to analyze the measured data and act upon the analyzed data. For example, the devices 202, 204, and 206 may be configured to modify therapy or provide alarm indications based on the analysis of the data.

In one embodiment, devices 202, 204, and 206 may also provide therapy. Therapy can be provided automatically or in response to an external communication. Devices 202, 204, and 206 can be programmable in that the characteristics of their sensing (e.g., duration and interval), therapy, or communication can be altered via communication between the devices 202, 204, and 206 and other components of the advanced patient management system 200. Devices 202, 204, and 206 can also perform self-checks or be interrogated by the communications system 210 to verify that the devices are functioning properly. Examples of different embodiments of the devices 202, 204, and 206 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of an implantable device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the advanced patient management system 200 may utilize other implantable devices as well that provide physiological measurements of the patient, such as drug pumps, neurological devices (e.g., stimulators), oxygen sensors, etc.

Derived measurements can also be determined from the implantable devices. For example, a sleep sensor can rely on measurements taken by an implanted accelerometer that measures body activity levels. The sleep sensor can estimate sleeping patterns based on the measured activity levels. Other derived measurements can include a functional capacity indicator, autonomic tone indicator, sleep quality indicator, cough indicator, anxiety indicator, and cardiovascular wellness indicator for calculating a quality of life indicator for quantifying a patient's overall health and well-being.

Devices 202, 204, and 206 can also be external devices, or devices that are not implanted in the human body, that may be used to measure physiological data. Such devices may include a multitude of devices to measure data relating to the human body, including temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System ("GPS")).

Devices 202, 204, and 206 can also be environmental sensors. The devices can be placed in a variety of geographic locations (in close proximity to patient or distributed throughout a population) and can record non-patient specific characteristics such as, for example, temperature, air quality, humidity, carbon monoxide level, oxygen level, barometric pressure, light intensity, and sound.

One or more of the devices 202, 204, and 206 (for example, device 206) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" and "Does this taste good?". The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being may emerge with a finer resolution than the quanta of the three responses.

The subjective data can be collected from the patient at set times, or, alternatively, can be collected whenever the patient feels like providing subjective data. The subjective data can also be collected substantially contemporaneously with physiological data to provide greater insight into overall patient wellness.

The device 206 can be any device that accepts input from a patient or other concerned individual and/or provides information in a format that is recognizable to the patient. Device 206 can typically include a keypad, mouse, display, handheld device, interactive TV, a cellular telephone or other radio frequency ("RF") communications device, cordless phone, corded phone, speaker, microphone, email message, and physical stimulus such as an electric shock or change in temperature or light intensity.

Figure 3:
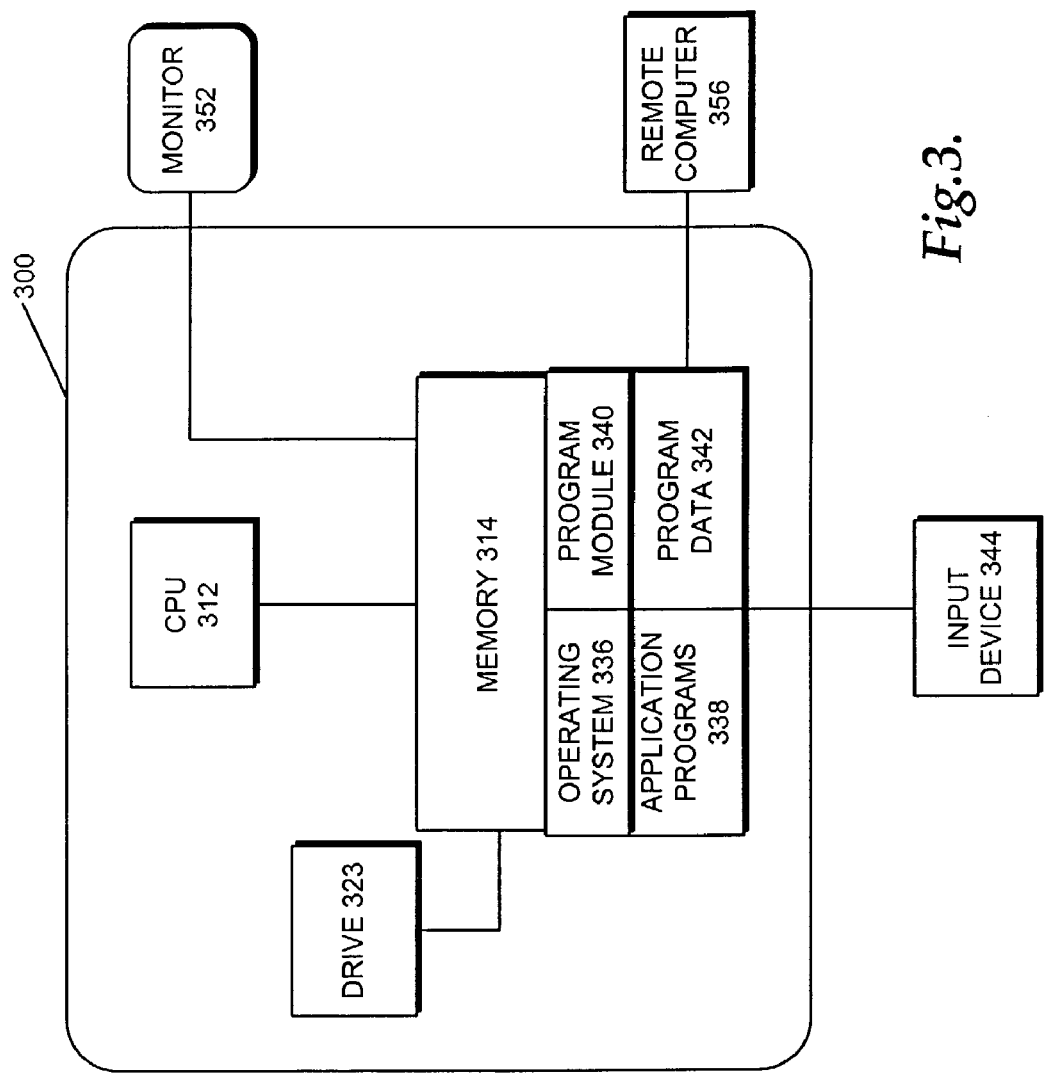
FIG. 3 is a block diagram illustrating a computer system utilized in various embodiments of the present invention.

In one example embodiment, the device 206 includes or is part of a computer system 300, as illustrated in FIG. 3. The computer system 300 can include a central processor unit 312 and a system memory 314. The computer system 300 further includes one or more drives 323 for reading data from and writing data to, as well as an input device 344 such as a keyboard or mouse and a monitor 352 or other type of display device.

A number of program modules may be stored on the drive 323, including an operating system 336, one or more application programs 338, other program modules 340, and program data 342. The computer system 300 may operate in a networked environment using logical connections to one or more remote computers or computer systems 356. Computer system 300 may also comprise a hand-held computer such as a personal digital assistant ("PDA") computer.

Figure 4A:
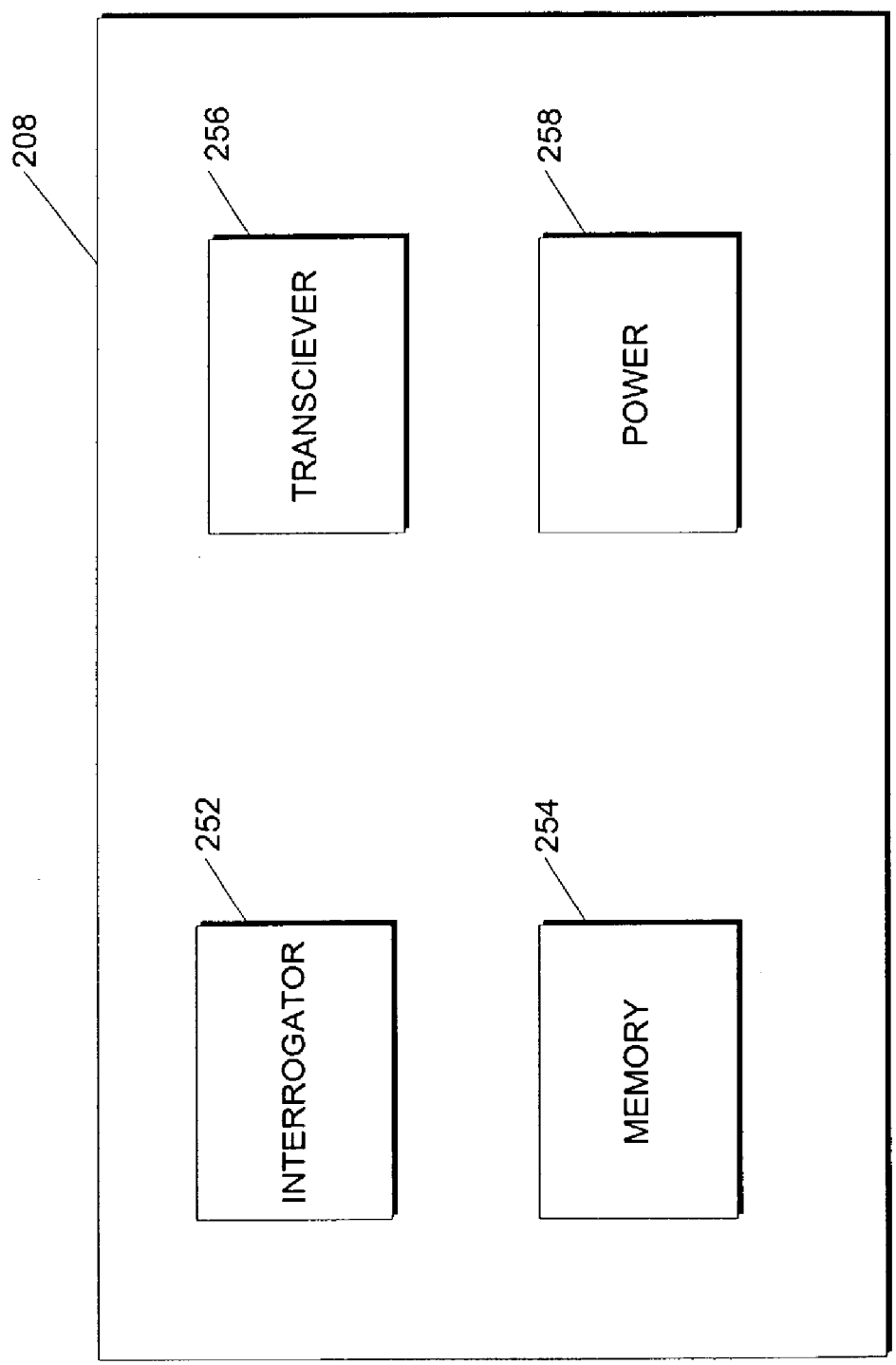
FIG. 4A is a block diagram illustrating an example interrogator/transceiver unit provided by one embodiment of the present invention.

Referring now to FIG. 4A, the advanced patient management system 200 may include one or more interrogator/transceiver units ("ITUs"), such as ITU 208. The ITU 208 includes an interrogator module 252 for receiving data from a device such as devices 202, 204, and 206, a memory module 254 for storing data, a transceiver module 256 for sending data both to the devices 202, 204, and 206 as well as other components of the advanced patient management system 200. The ITU 208 also includes a power module 258 that provides power.

The ITU 208 may perform one or more of the following functions: (1) data storage; (2) data analysis; (3) data forwarding; (4) patient interaction; and (5) patient feedback. For example, the ITU 208 may facilitate communications between the devices 202, 204, and 206 and the communications system 210. The ITU 208 can, periodically or in real-time, interrogate and download into memory clinically relevant patient data from the devices 202, 204, and/or 206. This data can include, in the cardiac sensor context, for example, P and R-Wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data may be sent to the ITU 208 by the devices 202, 204, and 206 in real-time or periodically uploaded out of buffers on the devices.

The ITU 208 may also allow for patient interaction. For example, the ITU 208 may include a patient interface and allow the patient to input subjective data. In addition, the ITU 208 may provide feedback to the patient based on the data that has been analyzed or based on information communicated by the communications system 210.

In another embodiment, the ITU 208 can include a telemetry link from the implanted device to a network that forms the basis of a wireless LAN in the patient's home. The device can systematically download information from the devices 202, 204, and 206 while the patient is sleeping, for example. The data can be transmitted by landline or wirelessly to the communications system 210 or directly to the host 212. In addition, in one embodiment the ITU 208 can function in a hybrid form, utilizing wireless communication when available and defaulting to landline communication when the wireless communication becomes unavailable.

Some devices, such as legacy implanted cardiac rhythm management ("CRM") devices, communicate via an internal telemetry transceiver that communicates with an external programmer. The communication range of such devices is typically 4–12 inches. Communications system 210 may include a special purpose "ITU" that communicates with an implanted legacy device, on one hand, and communicates with the wireless Internet on the other. Patients with legacy devices are provided with these ITUs and are instructed to use them periodically (e.g., monthly).

The ITU 208 may be in the form of a small device that is placed in an inconspicuous place within the patient's residence. Alternatively, the ITU may be implemented as part of a commonly used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 208 may comprise a hand-held device such as a PDA, cellular telephone, or other similar device that is in wireless communication with the devices 202, 204, and 206. The hand-held device may upload the data to the communications system 210 wirelessly. Alternatively, the hand-held device may periodically be placed in a cradle or other similar device that is configured to transmit the data to the communications system 210.

The ITU 208 can also perform analysis on the data and provide immediate feedback, as well as perform a variety of self-diagnostic tests to verify that it is functioning properly and that communication with the communications system 210 has not been compromised. For example, the ITU 208 can perform a diagnostic loop-back test, which involves sending a request through the communications system 210 to the host 212. The host 212 can then reply with a response back through the communications system 210 to the ITU 208. If a specific duration elapses before the ITU 208 receives the response, or if the ITU 208 receives an unexpected response, the ITU 208 can provide indications that the system is not functioning properly. For example, if wireless communications between the ITU 208 and the communications system 210 have been interrupted, and the ITU 208 performs a self-diagnostic test that fails, the ITU 208 may alert data management service personnel so that corrective action may be taken. Alternatively, the ITU 208 can sound a visual and/or audible alarm to alert the patient that communication has been interrupted. In another embodiment, the ITU 208 can automatically fail-back to a landline system to communicate with the communications system 210.

In other embodiments of the advanced patient management system 200, the ITU 208 can be eliminated completely, and the devices 202, 204, and 206 can communicate directly with the communications system 210 and/or host 212. For example, device 202 may include a miniature cellular phone capable of wirelessly uploading clinical data from the device on a periodic basis. This is particularly advantageous for devices that are mobile (e.g., an implanted device in a patient that is traveling). The device 202 can incorporate wireless telecommunications such as cellular, BLUETOOTH, or IEEE 802.11B to communicate with the communications system 210.

To conserve the energy of the devices 202, 204, and 206, particularly when the devices (e.g., device 202) are configured to communicate directly with the communications system 210 without using an ITU, in one example embodiment the devices are configured to communicate during a given duty cycle. For example, the device 202 can be configured to communicate with the communications system 210 at given intervals, such as once a week. The device 202 can record data for the time period (e.g., a week) and transmit the data to the communications system 210 during the portion of the cycle that transmission is active and then conserve energy for the rest of the cycle. In another example, the device 202 conserves energy and only communicates with the communications system 210 when an "interesting" event, such as a heart arrhythmia, has occurred. In this manner, device 202 can communicate directly with the communications system 210 and/or host 212 without using the ITU 208, while conserving the energy of the device by communicating only during a given duty cycle.

If multiple devices, such as devices 202, 204, and 206, are provided for a given patient, each device may include its own means for communicating with the ITU 208 or communications system 210. Alternatively, a single telemetry system may be implemented as part of one of the devices, or separate from the devices, and each device 202, 204, and 206 can use this single telemetry system to communication with the ITU 208 or the communications system 210.

In yet another embodiment, the devices 202, 204, and 206 include wires or leads extending from devices 202, 204, and 206 to an area external of the patient to provide a direct physical connection. The external leads can be connected, for example, to the ITU 208 or a similar device to provide communications between the devices 202, 204, and 206 and the other components of the advanced patient management system 200.

The advanced patient management system 200 can also involve a hybrid use of the ITU 208. For example, the a device such as devices 202, 204, and 206 can intelligently communicate via short-range telemetry with the ITU when the patient is located within the patient's home and communicate directly with the communications system 210 or host 212 when the patient is traveling. This may be advantageous, for example, to conserve battery power when the devices are located near an ITU.

Figure 4B:
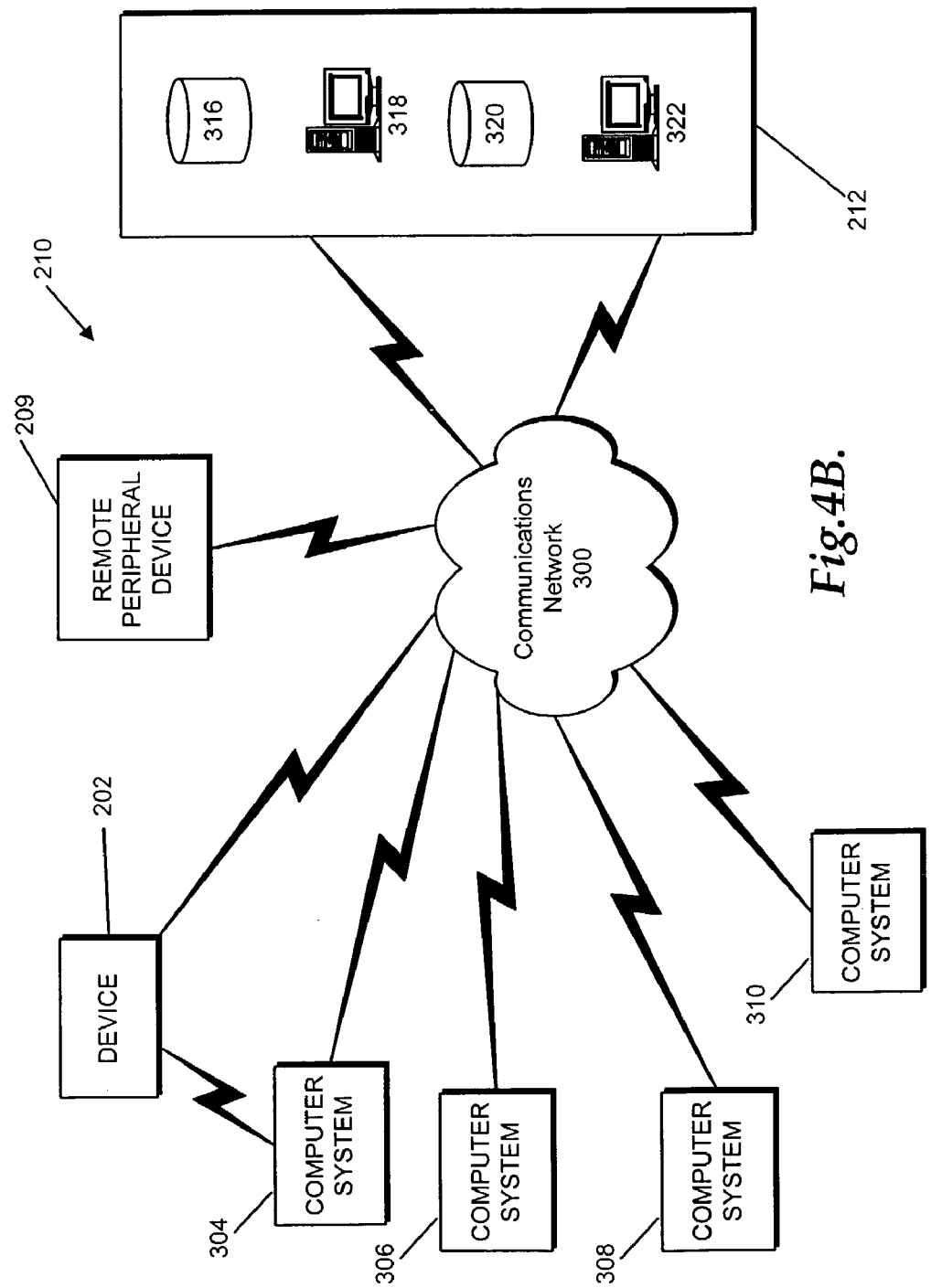
FIG. 4B is a block diagram showing a communication system utilized in one embodiment of the present invention.

Communications system 210 provides for communications between and among the various components of the advanced patient management system 200, such as the devices 202, 204, and 206, host 212, and remote peripheral devices 209. FIG. 4B illustrates communications system 210 according one embodiment of the present invention. The communications system 210 includes a plurality of computer systems 304, 306, 308, and 310, as well as device 202, host 212, and remote peripheral device 109, connect to one another by the communications network 300. The communications network 300 may be, for example, a local area network ("LAN"), wide area network (WAN), or the Internet. Communications among the various components, as described more fully below, may be implemented using wired or wireless technologies.

In the example embodiment illustrated, the host 212 includes server computers 318 and 322 that communicate with computers 304, 306, 308, and 310 using a variety of communications protocols, described more fully below. The server computers 318 and 322 may store information in databases 316 and 320. This information may also be stored in a distributed manner across one or more additional servers.

As shown in FIG. 4B, a variety of communication methods and protocols may be used to facilitate communication between devices 202, 204, and 206, ITU 208, communications system 210, host 212, and remote peripheral device 109. For example, wired and wireless communications may be used. Wired communication methods may include, for example and without limitation, traditional copper-line communications such as DSL, broadband technologies such as ISDN and cable modems, and fiber optics, while wireless communications may include cellular, satellite, radio frequency ("RF"), Infrared, etc.

For any given communication method, a multitude of standard and/or proprietary communication protocols may be used. For example and without limitation, wireless (e.g., radio frequency pulse coding, spread spectrum, direct sequence, time-hopping, frequency hopping, etc.) and other communication protocols (e.g., SMTP, FTP, TCP/IP) may be used. Other proprietary methods and protocols may also be used. Further, a combination of two or more of the communication methods and protocols may also be used.

The various communications between the components of the advanced patient management system 200 may be made securely using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 200. Encryption, authentication and verification techniques may also be used to detect and correct data transmission errors.

Communications among the various components of the advanced patient management system 200 may be enhanced using compression techniques to allow large amounts of data to be transmitted efficiently. For example, the devices 202, 204, and 206 may compress the information recorded from the patient prior to transmitting the information to the ITU 208 or directly to the communications system 210. The communication methods and protocols can facilitate periodic and/or real-time delivery of data.

The host 212 may include a database module 214, an analysis module 216, and a delivery module 218 (shown in FIG. 2). The host 212 preferably includes enough processing power to analyze and process large amounts of data collected from each patient, as well as to process statistics and perform analysis for large populations. For example, the host 212 may include a mainframe computer or multi-processor workstation. The host 220 may also include one or more commercial personal computer systems containing sufficient computing power and memory. The host 220 may include storage medium (e.g. hard disks, optical data storage devices, etc.) sufficient to store the massive amounts of high-resolution data that are collected from the patients and analyzed.

The host 212 may also include identification and contact information (e.g., IP addresses and/or telephone numbers) for the various devices communicating with it, such as ITU 208 and peripheral device 209. For example, each ITU 208 may be assigned a hard-coded or static identifier (e.g., IP address, telephone number, etc.), which would allow the host 212 to identify which patient's information the host 212 is receiving at a given instant. Alternatively, each device 202, 204, and 206 may be assigned a unique identification number, or a unique patient identification number may be transmitted with each transmission of patient data.

When a device is first activated, several methods may be used to associate data received by the advanced patient management system 200 with a given patient. For example, each device may include a unique identification number and a registration form that may be filled out by the patient, caregiver, or field representative. The registration form can be used to collect the necessary information to associate collected data with the patient. Alternatively, the user could logon to a web site to allow for the registration information to be collected. Another possible method involves including a barcode on each device that can be scanned prior to or in conjunction with initial measurements to provide information to associate the recorded data with the given patient.

Referring again to FIG. 2, the database module 214 can include a patient database 400, a population database 402, a medical database 404, and a general database 406, all described further below. The patient database 400 includes patient specific data, including data acquired by the devices 202, 204, and 206. The patient database 400 can also include a patient's medical records. The patient database 400 can include historical information regarding the devices 202, 204, and 206. For example, if device 202 is an ICD, the patient database 400 can record the following device information: P and R measurements, pacing frequency, pacing thresholds, shocking events, recharge time, lead impedance, battery voltage/remaining life, ATR episode and EGMs, histogram information, and other device information. The information stored in the database 400 can be recorded at various times depending on the patient requirements or device requirements. For example, the database 400 can be updated at periodic intervals that coincide with the patient downloading data from the device. Alternatively, data in the database 400 can be updated in real time. Typically, the sampling frequency will depend on the health condition being monitored and the co-morbidities.

The population database 402 includes non-patient specific data, such as data relating to other patients and population trends. The population database 402 also records epidemic-class device statistics and patient statistics. The population database 402 also includes data relating to staffing by health care providers, environmental data, pharmaceuticals, etc.

The medical database 404 includes clinical data relating to the treatment of diseases. For example, the medical database 404 can include historical trend data for multiple patients in the form of a record of progression of their disease(s) along with markers of key events.

The general database 406 includes non-medical data of interest to the patient. This can include information relating to news, finances, shopping, technology, entertainment, and sports. The general database 406 can be customized to provide general information of specific interest to the patient. For example, stock information can be presented along with the latest health information as detected from the devices 202, 204, and 206.

In another embodiment, information may also be provided from an external source such as external database 558. For example, the external database may include external medical records maintained by a third party, such as drug prescription records maintained by a pharmacy providing information related to what types of drugs have been prescribed for a patient. The analysis module 216 includes a patient analysis module 550, device analysis module 552, population analysis module 554, and learning module 556.

The patient analysis module 550 may utilize information collected by the advanced patient management system 200, as well as information for other relevant sources, to analyze data related to a patient and provide timely and predictive assessments of the patient's well-being. In performing this analysis, the patient device module 550 may utilize data collected from a variety of sources, include patient specific physiological and subjective data collected by the advanced patient management system 200, medical and historical records (e.g., lab test results, histories of illnesses, etc., drugs currently and previously administered, etc.), as well as information related to population trends provided from sources external to the advanced patient management system 200.

For example, in one embodiment, the patient analysis module 550 may make a predictive diagnosis of an oncoming event based on information stored in the database module 214. For example, the data continuously gathered from a device of a given patient at a heightened risk for a chronic disease event (such as de-compensations in heart failure) can be analyzed. Based on this analysis, therapy, typically device-based or pharmaceutical, can then be applied to the patient.

In another example embodiment, the patient analysis module 550 may provide a diagnosis of patient health status and predicted trend based on present and recent historical data collected from a device as interpreted by a system of expert knowledge derived from working practices within clinics. For example, the patient analysis module 550 may perform probabilistic calculations using currently collected information combined with regularly collected historical information to predict patient health degradation.

In another example embodiment, the patient analysis module 550 may conduct pre-evaluation of the incoming data stream combined with patient historical information and information from patients with similar disease states. The pre-evaluation system is based on data derived from working clinical practices and the records of outcomes. The derived data can be processed into a neural network or equivalent system to reflect the clinical practice. Further, the patient analysis module 550 may also provide means for periodic processing of present and historical data to yield a multidimensional health state indication along with disease trend prediction, next phase of disease progression co-morbidities, and inferences about what other possible diseases may be involved. The patient analysis module 550 may also integrate data collected from internal and external devices with subjective data to optimize management of overall patient health.

The device analysis module 552 analyzes data from the devices 202, 204, and 206 and ITU 208 to predict and determine device failures. For example, if an implanted device 202 fails to communicate at an expected time, device analysis module 552 determines the source of the failure and takes action to restore the performance of the device 202.

The device analysis module 552 may also perform additional deterministic and probabilistic calculations. For example, the device analysis module 552 may gather data related to charge levels within a given device, such as an ICD, and provide analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

The population analysis module 554 uses the data collected in the database module 214 to manage the health of a population. For example, a clinic managing cardiac patients can access the advanced patient management system 200 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 554 trends the patient population therapy and management as recorded by the devices and directs health care resources to best satisfy the needs of the population. The resources can include people, facilities, supplies, and/or pharmaceuticals. In other embodiments, the population analysis module. Can detect epidemics and other events that affect large population groups. The population analysis module 554 can issue alerts that can initiate a population quarantine, redirect resources to balance size of staffing with number of presenting population, and predict future need of qualified specialists.

The population analysis module 554 may utilize a variety of characteristics to identify like-situated patients, such as, for example, sex, age, genetic makeup, etc. The population analysis module 554 may develop large amounts of data related to a given population based on the information collected by the advanced patient management system 200. In addition, the population analysis module 554 may integrate information from a variety of other sources. For example, the population analysis module 554 may utilized data from public domain databases (e.g. National Institute of Health), public and governmental and health agency databases, private insurance companies, medical societies (e.g. American Heart Association), and genomic records (e.g., DNA sequences).

In one embodiment of the invention, the host 212 may be used as a "data clearinghouse," to gather and integrate data collected from the devices 202, 204, and 206, as well as data from sources outside the advanced patient management system 200. The integrated data can be shared with other interested entities, subject to privacy restrictions, thereby increasing the quality and integration of data available.

The learning module 556 analyzes the data provided from the various information sources, including the data collected by the advanced patient system 200 and external information sources. For example, the learning module 556 analyzes historical symptoms, diagnoses, and outcomes along with time development of the diseases and co-morbidities. The learning module 556 can be implemented via a neural network (or similar) system.

The learning module 556 can be partially trained (i.e., the learning module 556 may be implemented with a given set of preset values and then learn as the advanced patient management system functions) or untrained (i.e., the learning module 556 is initiated with no preset values and must learn from scratch as the advanced patient management system functions). In other alternative embodiments, the learning module 556 may continue to learn and adjust as the advanced patient management system functions (i.e., in real time), or the learning module 556 may remain at a given level of learning and only advanced to a higher level of understanding when manually allowed to do so.

The learning module 556 may implement various algorithms and mathematical modeling such as, for example, trend and statistical analysis, data mining, pattern recognition, cluster analysis, neural networks and fuzzy logic. Learning module 556 may perform deterministic and probabilistic calculations. Deterministic calculations include algorithms for which a clear correlation is known between the data analyzed and a given outcome. For example, there may be a clear correlation between the power left in a battery of an implantable device and the amount of time left before the battery must be replaced.

A probabilistic calculation involves the correlation between data and a given outcome that is less than 200 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 556 may perform probabilistic calculations and select a given response based on less than a 100% probability. Further, as the learning module 556 "learns" for previous determinations (e.g., through a neural network configuration), the learning module 556 may become more proficient at assigning probabilities for a given data pattern, thereby being able to more confidently select a given response. As the amount of data that has been analyzed by the learning module 556 grows, the learning module 556 may become more and more accurate at assigning probabilities based on data patterns. A bifurcated analysis may be performed for diseases exhibiting similar symptoms.

In addition, patient specific clinical information can be stored and tracked for hundreds of thousands of individual patients, enabling a first-level electronic clinical analysis of the patient's clinical status and an intelligent estimate of the patient's short-term clinical prognosis. The learning module 556 may be capable of tracking and forecasting a patient's clinical status with increasing levels of sophistication by measuring a number of interacting co-morbidities, all of which may serve individually or collectively to degrade the patient's health. This will enable learning module 556, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

In a neural network embodiment, new clinical information is presented to create new neural network coefficients that are distributed as a neural network knowledge upgrade. The learning module 556 can include a module for verifying the neural network conclusions for clinical accuracy and significance. The learning module 556 can analyze a database of test cases, appropriate outcomes and relative occurrence of misidentification of the proper outcomes. In some embodiments, the learning module 556 can update the analysis module 216 when the analysis algorithms exceed a threshold level of acceptable misidentifications.

The delivery module 218 coordinates the delivery of feedback based on the analysis performed by the host 212. In response to the analysis module 216, delivery module 218 can manage the devices 202, 204, and 206, perform diagnostic data recovery, program the devices, and otherwise deliver information as needed.

In some embodiments, the delivery module 218 can manage a web interface that can be accessed by patients or caregivers. The information gathered by an implanted device can be periodically transmitted to a web site that is securely accessible to the caregiver and/or patient in a timely manner. In other embodiments a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as MY YAHOO provided by YAHOO! INC. of Sunnyvale, Calif. A patient can access his or her MY YAHOO homepage and receive information regarding current health and trends derived from the information gathered from the devices 202, 204, and 206, as well as other health information gathered from other sources. The patient may also access information other than health information on the MY YAHOO website, such as weather and stock market information. Other electronic delivery methods such as email, facsimile, etc. can also be used.

In an alternative embodiment, the data collected and integrated by the advanced patient system 200, as well as any analysis performed by the system 200, can be delivered by delivery module 218 to a caregiver's hospital computer system for access by the caregiver. A standard or custom interface can facilitate communications between the advanced patient management system 200 and a legacy hospital system used by the caregiver so that the caregiver can access all relevant information using a system familiar to the caregiver.

In addition, the advanced patient management system 200 can be configured so that various components of the system (e.g., ITU 208, communications system 210, and/or host 212) provide reporting to various individuals (e.g., patient and/or caregiver). For example, different levels of reporting can be provided by (1) the ITU 208 and (2) the host 212. For example, the ITU 208 may be configured to conduct rudimentary analysis of data gathered from devices 202, 204, and 206, and provide reporting should an acute situation be identified. For example, if the ITU 208 detects that a significant heart arrhythmia is imminent or currently taking place, the ITU 208 can provide reporting in the form of an audible or visual alarm.

The host 212 can provide a more sophisticated reporting system. For example, the host 212 may provide exception-based reporting and alerts that categorize different reporting events based on importance. Some reporting events may not require caregiver intervention and therefore can be reported automatically. In other escalating situations, caregiver and/or emergency response personnel may need to become involved. For example, based on the data collected by the advanced patient management system 200, the delivery module 218 can communicate directly with the devices 202, 204, and 206, contact a pharmacy to order a specific medication for the patient, and/or contact 911 emergency response. In an alternative embodiment, the delivery module 218 and/or the patient may also establish a voice communication link between the patient and a caregiver, if warranted.

In addition to forms of reporting including visual and/or audible information, the advanced patient management system 200 can also communicate with and reconfigure one or more of the devices 202, 204, and 206. For example, if device 202 is part of a cardiac rhythm management system, the host 212 and communicate with the device 202 and reconfigure the therapy provided by the cardiac rhythm management system based on the data collected from one or more of the devices 202, 204, and 206. In another embodiment, the delivery module 218 can provide to the ITU 208 recorded data, an ideal range for the data, a conclusion based on the recorded data, and a recommended course of action. This information can be displayed on the ITU 208 for the patient to review.

The advanced patient management system 200 may also include one or more remote peripheral devices 209. The remote peripheral device 209 may include, for example and without limitation, cellular telephones, pagers, PDA devices, facsimiles, remote computers, printers, video and/or audio devices, etc. The remote peripheral device 209 may communicate using landline or wireless technologies and may be used by the patient or caregiver to communicate with the communications system 210 and/or the host 212. For example, the remote peripheral device 209 may be used by a caregiver to receive alerts from the host 212 based on data collected from the patient and to send instructions from the caregiver to either the patient or other clinical staff. In another example, the remote peripheral device 209 may be used by the patient to receive periodic or real time updates and alerts regarding the patient's health and well-being.

Figure 5:
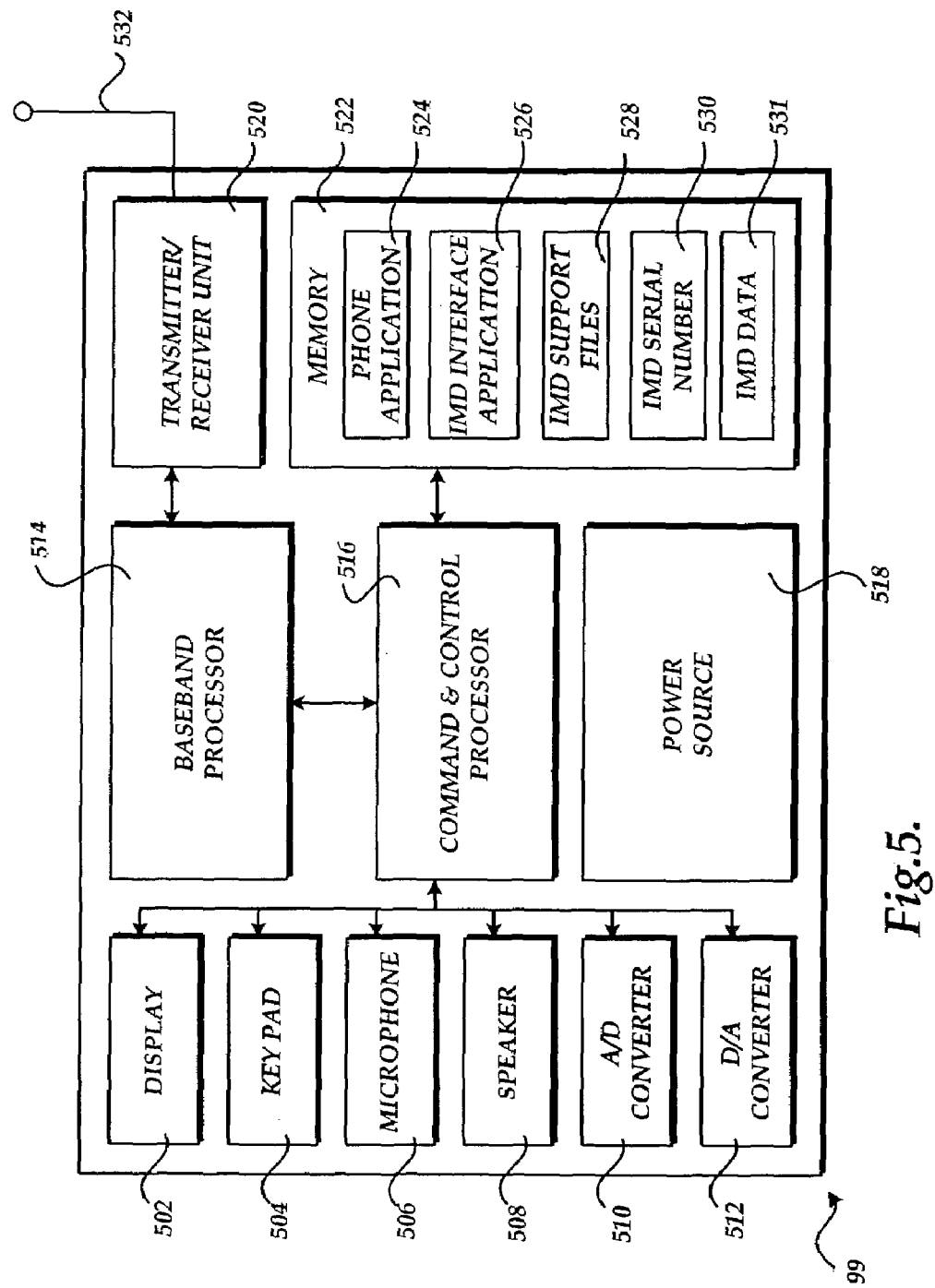
FIG. 5 is a block diagram showing a hardware architecture for an apparatus for enabling data communication between an IMD and a host computer provided according to one actual embodiment of the present invention.

Referring now to FIG. 5, an illustrative hardware architecture for an interface device 99 will be described. As described briefly above with respect to FIG. 1A, the interface device 99 comprises a wireless communication device capable of communicating with a host computer 200 via a long range communications link 104 and of communicating with an IMD 100 via a short range communications link 103. More particularly, according to the embodiment of the invention described herein, the interface device 99 comprises a digital wireless telephone modified for communication with the IMD 100 and for communicating with the host computer 200.

In order to provide these functions, the interface device 99 comprises a command and control processor 516 for controlling the operation of the interface device 99. As known to those skilled in the art, the command and control processor 516 may be embodied by any of a number of central processing unit devices. A memory 522 is used in conjunction with the command and control processor 516. The memory 522 stores a number of application and data files utilized for communicating with the host computer 200 and the IMD 100.

In particular, the memory 522 stores a phone application 524. The phone application 524 controls the operation of the interface device 99 when the device is utilized as a conventional wireless telephone. In this manner, the interface device 99 may be utilized to send and receive calls in a conventional manner through the long range wireless communications link 104. Aspects of the phone application 524 are well known to those skilled in the art.

The memory 522 also comprises an IMD interface application 526. The IMD interface application 526 is a time-sliced software application that executes concurrently with the phone application 524. As will be described in greater detail below with reference to FIG. 6, the IMD interface application 526 provides functionality for communicating with the IMD 100, interrogating the IMD 100 for clinical data, and for transmitting the clinical data received from the IMD 100 to the host computer 200 via the long range communications link 104. The IMD interface application 526 is described in detail below with reference to FIG. 6.

The memory 522 also includes IMD support files 528. The IMD support files 528 describe communication protocols for communicating with different types of IMD 100 devices. In this manner, the interface device 99 may be programmed to communicate with previously released IMD devices 100 and IMDs 100 to be released in the future. The particular IMD support file to be utilized with a given IMD 100 may be selected through the keypad 504 and the display 502, or through the use of an external programmer.

The memory 522 also stores an IMD serial number 530. The IMD serial number 530 comprises a hardware serial number for the IMD 100. The IMD serial number 530 may be utilized by the interface device 99 for gaining secure access to the memory contents of the IMD 100. Moreover, by keying the IMD serial number 530 to a hardware serial number of the IMD 100, a secure interface can be provided between the interface device 99 and the IMD 100. Other interface devices 99 not having the proper serial number for gaining access to the IMD 100 would not be permitted to engage in any form of communication with the IMD 100.

The memory 522 also stores IMD data 531. IMD data 531 comprises data received from the IMD 100. This data may include data regarding the characteristics of the patient's 102 body and data regarding the operation of the IMD 100. As used herein, the term "clinical data" refers to both data describing the physical condition of the patient 102 and data describing the operation of the IMD 100.

The hardware architecture of the illustrative interface device 99 also comprises a transmitter/receiver unit 520. The transmitter/receiver unit 520, or transceiver, comprises a frequency and protocol agile transmitter and receiver unit. The transceiver 520 is capable of configuring itself for communication with the IMD 100 via the short range communications link 102. The transceiver 520 is also capable of configuring itself for communications with the host computer 200 via the long range communication link 104. Moreover, in the embodiment of the invention described herein, the transceiver 520 is capable of configuring itself for voice communication with a wireless telephone network over the long range communications link 104. It should be appreciated that the function of the transceiver 520 may be performed by other types of devices.

Configuration of the transceiver 520 is performed under control of the IMD interface application 526. As will be described in greater detail below with respect to FIG. 6, the IMD interface application 526 may configure the transceiver 520 for communication with the IMD 100 on a predetermined schedule. Once the transceiver 520 has been configured for communication with the IMD 100, the IMD interface application 526 may interrogate the IMD 100 for stored clinical data. The clinical data received from the IMD 100 may then be stored as IMD data 531 in the memory 522. Once the clinical data has been received from the IMD 100, the IMD interface application 526 may reconfigure the transceiver 520 for use via the long range communications link 104.

The IMD interface application 526 is also operative to periodically determine whether IMD data 531 is stored in the memory 522 that has not been transmitted to the host computer 200. If the IMD interface application 526 makes such a determination, the IMD interface application 526 is further operative to establish a connection between the interface device 99 and the host computer 200 over the long range communications link 104. The IMD data 531 may then be transmitted from the interface device 99 to the host computer 200. If the IMD data 531 is successfully transmitted to the host computer 200, the IMD interface application 526 may remove the stored IMD data 531 from the memory 522. A schedule may be coordinated between the interface device 99 and the host computer 200 for providing a predetermined time at which the IMD data 531 should be transmitted.

The interface device 99 also includes a baseband processor 514 for setting up the long range communications link 104. As known to those skilled in the art, the baseband processor 514 is responsible for negotiating frequencies with the MTSO 110 and otherwise maintaining the communications link for voice and data communications over the long range communications link 104.

The interface device 99 also includes a keypad 504 for providing input to the interface device 99 and a display 502 for generating output. The interface device 99 also includes a microphone 506 and a speaker 508 for use during voice calls over the long range communications link 104. An analog-to-digital converter 510 and a digital-to-analog converter 512 are also provided as a part of the interface device 99 for converting spoken signals to digital data and for converting digital data to analog signals that may be played back on the speaker 508, respectively. Other conventional components may be provided as part of the interface device 99 for enabling voice and digital data communication over the long range communication link 104.

Figure 6:
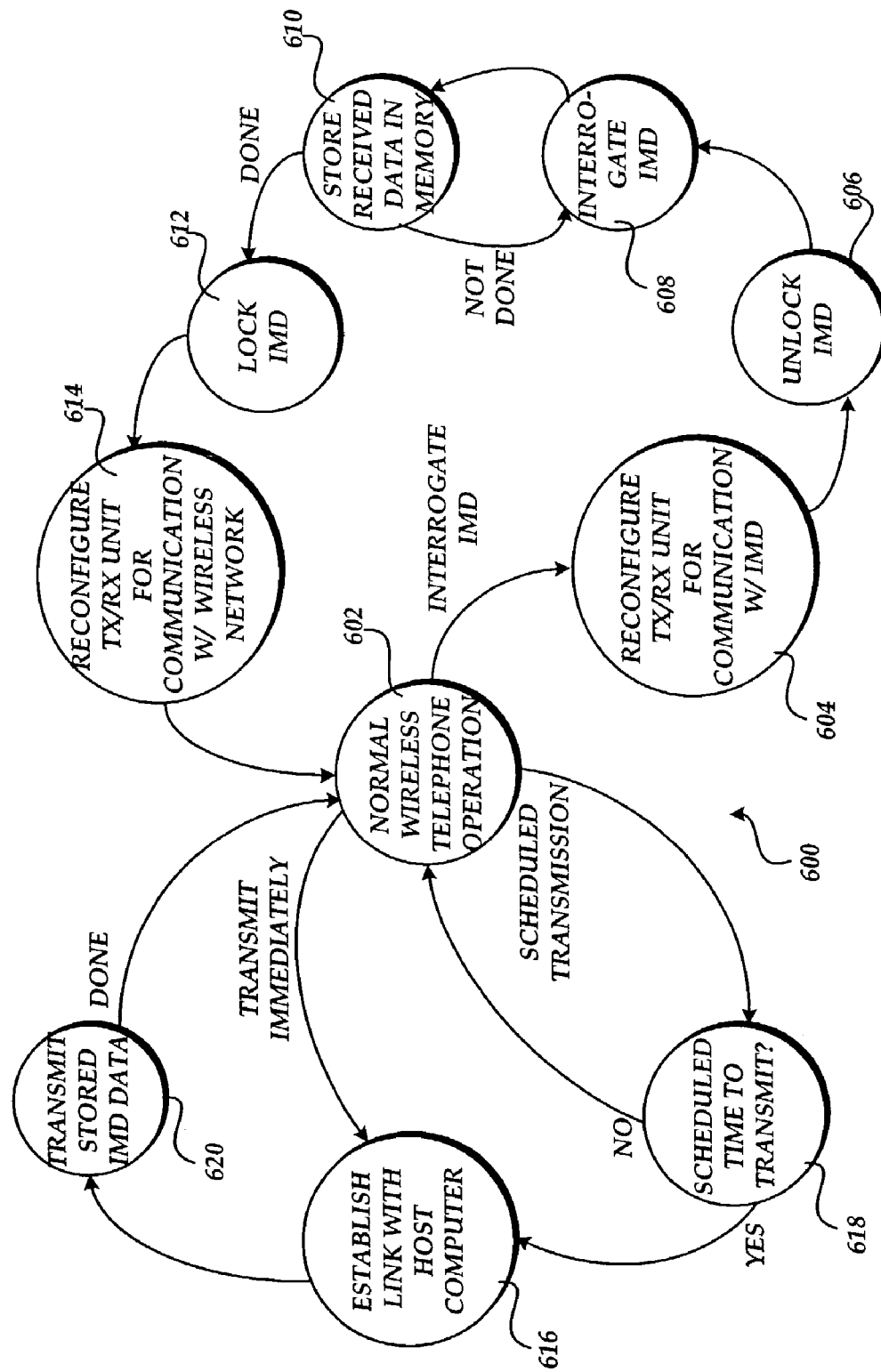
FIG. 6 is a state diagram illustrating a method for enabling data communication between an IMD and a host computer provided in one embodiment of the present invention.

Referring now to FIG. 6, a state machine 600 will be described illustrating the operation of the interface device 99. The state machine 600 begins in a home state 602, where the interface device 99 operates as a digital wireless telephone. As mentioned above, according to the embodiment of the present invention described herein, the interface device 99 comprises a digital wireless telephone modified for communication with the IMD 100 and the host computer 200. However, it should be appreciated by those skilled in the art that the interface device 99 may comprise other types of wireless digital devices such as two-way pagers and the like capable of communicating over a wireless communications network with a host computer 200.

At the home state 602, the interface device 99 is operative to send and receive wireless telephone calls over the long range telecommunications link 104. The interface device 99 is also operative to provide other types of conventional features provided by a wireless digital telephone. While in the home state 602, the interface device 99 is also operative to periodically interrogate the IMD 100 under control of the IMD interface application 526. The interrogation of the IMD 100 by the interface device 99 may occur according to a predefined schedule coordinated with the IMD 100, or other type of schedule set by a user. When the appointed time for interrogating the IMD 100 occurs, the state machine 600 transitions from state 602 to state 604.

At state 604, the IMD interface application 526 reconfigures the transceiver 520 for communication with the IMD 100 via the short range communication link 103. As a result, the interface device 99 is incapable of communicating via the long range communications link 104 while the IMD 100 is being interrogated. According to another embodiment of the invention, two transceivers are provided, with one being dedicated to communicating with the IMD 100 and another dedicated to wireless digital communication via the long range communication link 104. In this manner, communications over the long range communication link 104 may take place concurrently with the interrogation of the IMD 100.

From state 604, the state machine 600 transitions to state 606, where the IMD 100 is unlocked. An authentication procedure may be utilized by the interface device 99 to unlock and communicate with the IMD 100 in a secure manner. For instance, the IMD serial number 530 may be communicated to the IMD 100 to authenticate the interface device 99 for communication. Once the IMD 100 has been unlocked, the state machine 600 transitions to state 608.

At state 608, the interface device 99 interrogates the IMD 100 for clinical data stored within the IMD 100. The state machine 600 then transitions to state 610 where the clinical data received from the IMD 100 is stored within the memory 522 as IMD data 531. If additional data remains to be received within the IMD 100, the state machine 600 transitions back to state 608 where the interface device 99 continues to interrogate the IMD 100. Once all the clinical data residing within the IMD 100 has been received by the interface device 99, the state machine 600 transitions to state 612.

At state 612, the IMD 100 is locked in a secure manner by the interface device 99. The state machine 600 then transitions to state 614, where the transceiver 520 is reconfigured by the IMD interface application 526 for communication over the long range communications link 104. In this manner, the interface device 99 is reconfigured for digital voice and data communications over the long range wireless link 104. The state machine 600 then returns back to the home state 602 where normal wireless telephone operation is resumed.

From the home state 602, the interface device 99 also periodically establishes a communications link with the host computer 200 for transmission of the clinical data received from the IMD 100. The interface device 99 may transmit clinical data received from the IMD 100 to the host computer 200 immediately after receiving the information if the clinical data concerns a serious medical condition or a malfunction of the IMD 100. Alternatively, if the clinical data received from the IMD 100 is routine status data that does not relate to a serious medical condition or a malfunction, the interface device 99 may transmit the clinical data to the host computer 200 based upon a predetermined schedule. The predetermined schedule may be based upon, among other things, the line charges for utilizing the long range communications link 104. For instance, the interface device 99 may wait until off-peak hours when airtime rates are low to transmit the clinical data to the host computer 200. Those skilled in the art should appreciate that the schedule for communication between the interface device 99 and the host computer 200 may also be based upon other types of factors.

If, at the home state 602, the interface device 99 determines that the memory 522 contains IMD data 531 that must be transmitted to the host computer 200 immediately, the state machine 600 transitions to state 616. At state 616, the interface device 99 establishes a communications link with the host computer 200 via the long range communications link 104. The state machine 600 then transitions from state 616 to state 620 where the stored IMD data 531 is transmitted to the host computer 200 via the long range communications link 104. When the transmission has completed, the state machine 600 returns to the home state 602.

In order for a scheduled transmission to be made from the interface device 99 to the host computer 200, the state machine 600 transitions from state 602 to state 618. At state 618, the interface device 99 determines whether the current time is a scheduled time to transmit the IMD data 531 to the host computer 200. If the current time is not a scheduled time to transmit the clinical data, the state machine 600 returns to the home state 602. If, however, at state 618 the interface device 99 determines that the current time is a scheduled time to transmit, the state machine 600 transitions to state 616. As described above, the interface device 99 establishes a communications link with the host computer at state 616. The clinical data is then transmitted from the interface device 99 to the host computer 200 at state 620. When the interface device 99 has completed the transmission of the clinical data, the state machine 600 returns to the home state 602, where normal wireless telephone operation resumes.

Figure 7:
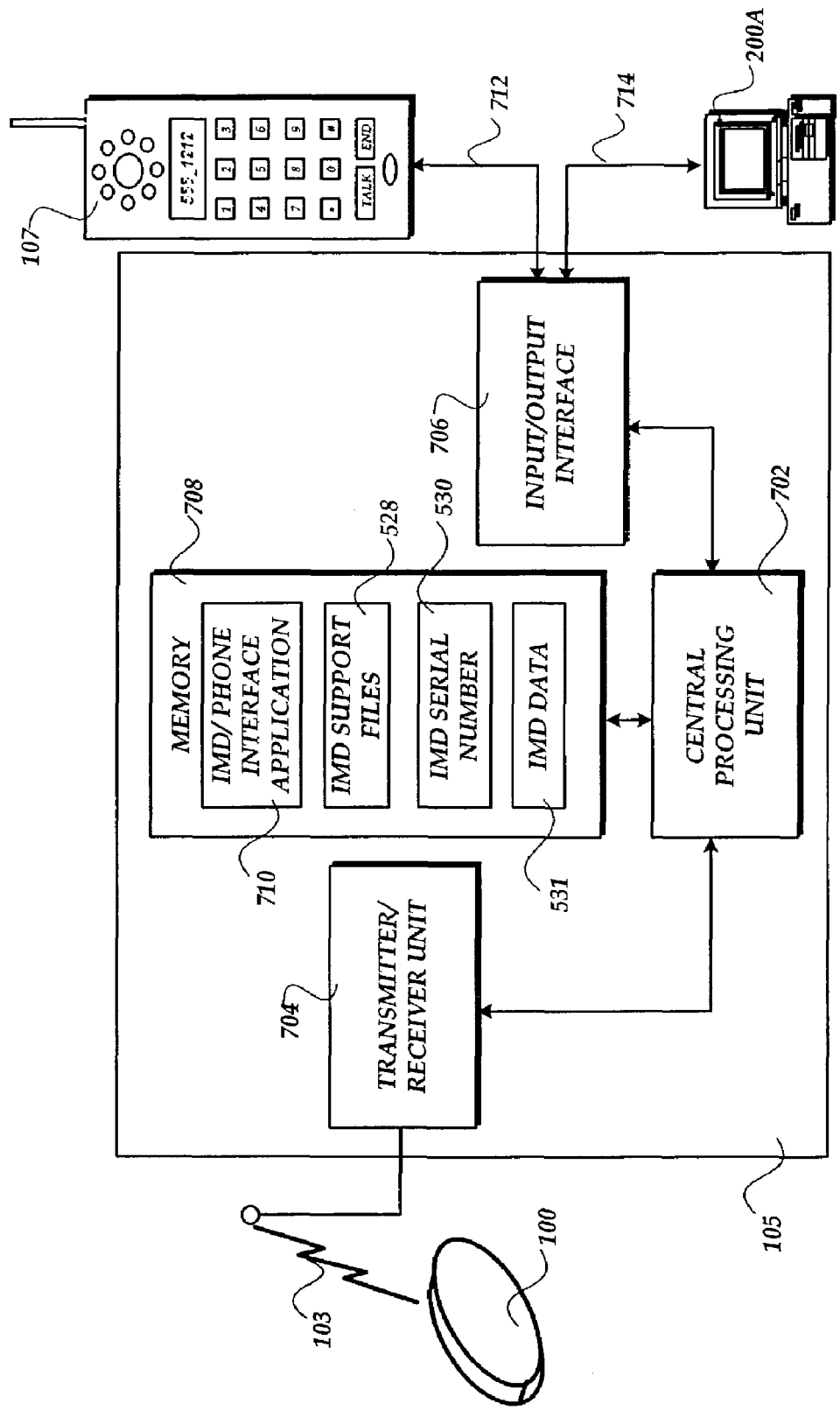
FIG. 7 is a block diagram showing a hardware architecture for an interface between an IMD and a communications device provided in one embodiment of the present invention.

Referring now to FIG. 7, an interface device 105 will be described according to another embodiment of the present invention. As described briefly above, in this embodiment of the present invention, the interface device 105 is operative to provide an interface between an IMD 100 and a host computer 200 through the use of a standard, unmodified wireless digital telephone 107. In order to provide such an interface, the interface device 105 comprises a transmitter/receiver unit 704, also called a transceiver, capable of establishing a short range communications link 103 with the IMD 100. Through the short range communications link 103, the interface device 105 can interrogate the IMD 100 and retrieve clinical data stored within the IMD 100.

The transceiver 704 is operated under control of a central processing unit 702. A memory 708 is also provided that stores a program and support files for enabling communication between the IMD 100 and the host computer 200. In particular, the memory 708 stores an IMD/phone interface application 710. The IMD/phone interface application 710 controls the operation of the interface device 105. In particular, the IMD/phone interface application 710 controls communication with the IMD 100 and the wireless digital telephone 107. Moreover, the IMD/phone interface application 710 controls the communication channel between the interface device 105 and the host computer 200. Additional details regarding the operation of the IMD/phone interface application 710 are described below with respect to FIG. 8.

The memory 708 also stores IMD support files 528, IMD serial number 530, and IMD data 531. As described above with respect to FIG. 5, the IMD support files 528 include data necessary to enable communications between any type of IMD 100 and the interface device 105. The data contained within the IMD support files 528 includes data regarding the protocols and communication frequencies utilized by different IMDs 100. The IMD serial number 530 may be used in an authentication procedure to gain secure access to the data stored within the IMD 100. The IMD data 531 comprises data retrieved from the IMD 100 by the interface device 105. The IMD data 531 is also referred to herein as clinical data.

The interface device 105 also comprises an input/output ("I/O") interface 706. The I/O interface 706 is connected to the central processing unit 702 and provides an interface to the wireless digital telephone 107 and a computer 200A. The I/O interface 706 may provide an interface to the wireless digital telephone 107 through a connection 712. The connection 712 may comprise a serial connection, a USB connection, or other type of connection utilized by wireless telephone manufacturers.

The I/O interface 706 also provides a connection 714 to a computer 200A. The computer 200A may comprise a standard personal computer operative to execute a programming application for configuring the interface device 105 for use with a particular IMD 100. In particular, the computer 200A may be utilized to select a particular IMD support file, to enter an IMD serial number 530, and to otherwise configure the interface device 105. The connection 714 between the I/O interface 706 and the computer 200A may comprise a serial connection, a USB connection, a FIREWIRE connection, or other type of standard I/O connection known to those skilled in the art.

According to one actual embodiment of the present invention, the interface device 105 is mechanically attached to the wireless digital telephone 107. The interface device 105 is configured in such a maimer that it is conformal to the wireless digital telephone 107. In this manner, the interface device 105 may be attached to the wireless digital telephone 107 and electrically connected through the connection 712. Moreover, the interface device 105 may be configured in a manner that allows the wireless digital telephone 107 to be placed in a standard charging cradle without modification. The interface device 105 may also be manufactured in a way that enables it to be semi-permanently attached to the wireless digital telephone 107 and mechanically rugged.

Figure 8:
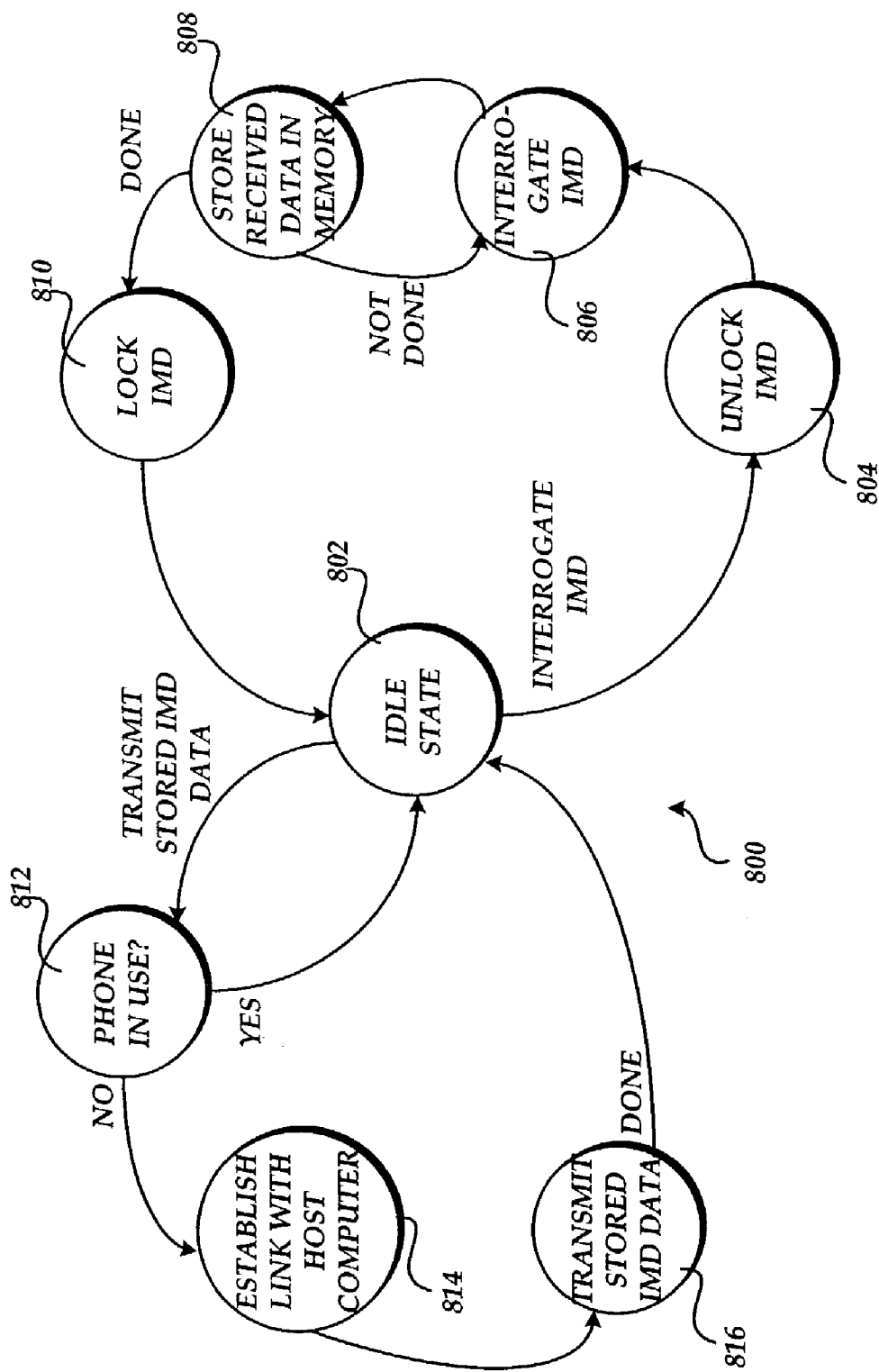
FIG. 8 is a state diagram illustrating aspects of a method for enabling communication between an IMD and a host computer provided according to one embodiment of the present invention.

Referring now to FIG. 8, a state machine 800 will be described illustrating the operation of the interface device 105. As described above, the interface device 105 is operated by the central processing unit 702 in conjunction with the IMD/phone interface application 710. The IMD/phone interface application 710 begins operation in an idle state 802. Periodically, the IMD/phone interface application 710 will establish a short range communications link 103 with the IMD 100 and interrogate the IMD 100. The interrogation may occur at a time predetermined and scheduled between the interface device 105 and the IMD 100. When the scheduled time for interrogation arrives, the state machine 800 transitions to state 804 where the interface device 105 unlocks the IMD 100. As described above, an authentication procedure may be utilized to provide secure access to the IMD 100. Accordingly to one embodiment of the present invention, the interface device 105 provides the IMD serial number 530 to the IMD 100 to authenticate itself. If the IMD 100 is successfully unlocked by the interface device 105, the state machine 800 transitions to state 806.

At state 806, the interface device 105 interrogates the IMD 100 to retrieve the clinical data stored within the IMD 100. In order to interrogate the IMD 100, the transmitter/receiver unit 704 communicates with the IMD 100 via the short range communications link 103. When data is received from the IMD 100, the state machine 800 transitions to state 808. At state 808 the clinical data received from the IMD 100 is stored in the memory 708. If additional clinical data remains within the IMD 100 to be retrieved, the state machine returns to state 806, where the interface device 105 continues to interrogate the IMD 100. When all of the clinical data has been retrieved from the IMD 100, the state machine 800 transitions to state 810 where the IMD 100 is locked. The state machine 800 then returns back to the idle state 802.

From the idle state 802, the IMD/phone interface application 702 periodically transmits IMD data 531 to the host computer 200 through the wireless digital telephone 107. The time for transmission of the clinical data from the interface device 105 to the host computer 200 may be based on a schedule predetermined between the interface device 105 and the host computer 200 or based upon the type of clinical data to be delivered. For instance, clinical data relating to normally delivered status information and non-critical patient information may be delivered on a predetermined schedule. However, information relating to a critical failure of the IMD 100 or to a serious health condition encountered by the patient 102 may be delivered immediately after it is retrieved from the IMD 100.

In order to transmit IMD data 531 from the interface device 105 to the host computer 200, the state machine 800 transitions from the idle state 802 to state 812. At state 812, the interface device 105 determines through the I/O interface 706 whether the wireless digital telephone 107 is currently in use. If the wireless digital telephone 107 is currently in use, the state machine 800 returns to the idle state 802. The interface device 105 may then wait a predetermined period of time before again attempting to transmit the IMD data 531.

If, at state 812, the interface device 105 determines that the wireless digital telephone 107 is not in use, the state machine transitions to state 814. At state 814, the interface device 105 initiates a connection with the host computer through the I/O interface 706, the connection 712, and the wireless digital telephone 107. As described above, the wireless telephone 107 may utilize a long range wireless communications link 104 to establish communication with the host computer 200. Once the communications channel has been established, the state machine 800 transitions to state 816.

At state 816, the clinical data stored within the interface device 105 is transmitted to the host computer 200. Once the clinical data has been transmitted from the interface device 105 to the host computer 200, the clinical data stored within interface 105 is deleted. The data delivered to the host computer 200 may also include a telephone number for the wireless digital telephone 107 so that the patient management system may contact a caregiver, emergency services, a physician, or the patient if the delivered data indicates a critical medical condition. From state 816, the state machine 800 returns to the idle state 802.

Based upon the foregoing, it should be appreciated that the present invention provides methods and apparatus for enabling communication between an IMD and a host computer. Although the invention has been described in language specific to computer structural features, methodological acts and by computer readable media, it is to be understood that the invention defined in the appended claims is not necessarily limited to the specific structures, acts or media described. Therefore, the specific structural features, acts and mediums are disclosed as exemplary embodiments implementing the claimed invention. Since many embodiments of the invention can be made without departing from the spirit and scope of the invention, the invention resides in the claims hereinafter appended.

We claim:

1. An apparatus for enabling data communication between an implantable medical device and a host computer, comprising:
   a central processing unit;
   a memory; and
   a transceiver capable of communicating with the implantable medical device via a short range wireless communications link;
   an input and output interface capable of interfacing with a communications device and establishing a communication link with the host computer via the communications device; and
   a program capable of executing on the central processing unit operative to:
      store a serial number corresponding to the implantable medical device in the memory,
      transmit the serial number to the implantable medical device as a part of an authentication procedure,
      receive clinical data stored in the implantable medical device via the short range wireless communications link,
      determine whether clinical data is stored in the memory,
      in response to determining that clinical data is stored in the memory, establish the communications link with the host computer via the communications device, and
      transmit the clinical data to the host computer.

2. The apparatus of claim 1, in which the transceiver is a frequency and protocol agile transceiver capable of:
   configuring itself for communication with the implantable medical device using a short range wireless communications link; and
   reconfiguring itself for communication with the host computer using a long range wireless communications link.

3. The apparatus of claim 1 in which the program is operative to:
   configure the transceiver for communication with the implantable medical device, and
   store the clinical data in the memory for subsequent delivery to the host computer via the long range wireless communications link.

4. The apparatus of claim 3, wherein the program is further operative to configure the transceiver for communication with the host computer via the long range wireless communications link.

5. The apparatus of claim 4, wherein the program is further operative to:
   determine whether the clinical data was successfully transmitted to the host computer; and to
   remove the clinical data from the memory if the clinical data was successfully transmitted to the host computer.

6. The apparatus of claim 5, wherein the program is further operative to:
   transmit the clinical data to the host computer on a schedule coordinated with the host computer.

7. The apparatus of claim 3, wherein the program is further operative to:
   configure the transceiver for communication with the host computer via the long range wireless communications link;
   determine whether the clinical data should be immediately delivered to the host computer if the clinical data is stored in the memory; and
   in response to determining that the clinical data should be immediately delivered to the host computer, to immediately establish a data communications channel with the host computer via the long range wireless communications link and to transmit the clinical data to the host computer via the channel.

8. The apparatus of claim 1, wherein the program is further operative to:
   store in the memory implantable medical device support files describing protocols for communicating with a plurality of different types of implantable medical devices, and
   utilize said support files to communicate with said plurality of different types of implantable medical devices.

9. The apparatus of claim 1, wherein the apparatus is powered by the communications device.

10. The system of claim 1, the transceiver comprising a frequency and protocol agile single transceiver capable of being configured to both:
   communicate with the implantable medical device using a short range wireless communication protocol, and
   communicate with the host computer using a long range wireless communication protocol.

11. A method for enabling data communication between an implantable medical device and a host computer, comprising:
   configuring a transceiver for wireless communication with the implantable medical device using a short range wireless communications link;
   storing a serial number corresponding to the implantable medical device in a memory of the transceiver;
   transmitting the serial number to the implantable medical device as part of an authentication procedure;
   receiving clinical data from the implantable medical device via the transceiver;
   determining whether clinical data is stored in the memory of the transceiver;
   in response to determining that clinical data is stored in the memory, configuring the transceiver for communication with the host computer using a long range wireless communications link; and
   transmitting the clinical data to the host computer via the long range wireless communications link.

12. The method of claim 11, further comprising:
   determining whether the clinical data should be immediately delivered to the host computer; and
   in response to determining that the clinical data should be immediately delivered to the host computer, immediately transmitting the clinical data to the host computer via the long range wireless communications link.

13. The method of claim 12, further comprising:
   storing the clinical data for subsequent delivery to the host computer in response to determining that the clinical data should not be immediately delivered to the host computer.

14. The method of claim 13, further comprising:
   transmitting the stored clinical data to the host computer via the long range wireless communications link on a schedule coordinated with the host computer.

* * * * *